United States Patent
Ziegle et al.

(10) Patent No.: US 11,439,308 B2
(45) Date of Patent: Sep. 13, 2022

(54) METHODS AND SYSTEMS FOR THERMAL MONITORING OF TISSUE WITH AN ULTRASOUND IMAGING SYSTEM

(71) Applicant: GE Precision Healthcare LLC, Milwaukee, WI (US)

(72) Inventors: Jens Ziegle, Magdeburg (DE); Alfredo Guillermo Illanes Manríquez, Magdeburg (DE); Elmer Jeto Gomes Ataide, Magdeburg (DE); Michael Friebe, Recklinghausen (DE)

(73) Assignee: GE Precision Healthcare LLC, Milwaukee, WI (US)

( * ) Notice: Subject to any disclaimer, the term of this patent is extended or adjusted under 35 U.S.C. 154(b) by 135 days.

(21) Appl. No.: 16/927,685

(22) Filed: Jul. 13, 2020

(65) Prior Publication Data
US 2022/0007946 A1    Jan. 13, 2022

(51) Int. Cl.

| | |
|---|---|
| *A61B 5/01* | (2006.01) |
| *G06K 9/00* | (2022.01) |
| *G06T 7/00* | (2017.01) |
| *G06V 10/42* | (2022.01) |
| *G06V 10/52* | (2022.01) |

(52) U.S. Cl.
CPC .......... *A61B 5/015* (2013.01); *G06K 9/00563* (2013.01); *G06T 7/0014* (2013.01); *G06V 10/431* (2022.01); *G06V 10/52* (2022.01); *G06T 2207/10132* (2013.01); *G06T 2207/20064* (2013.01); *G06T 2207/20104* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 7,367,944 B2 * | 5/2008 | Rosemberg | A61B 8/0833 600/439 |
| 8,376,946 B2 * | 2/2013 | Littrup | A61B 8/4483 600/437 |

(Continued)

FOREIGN PATENT DOCUMENTS

WO    2019161914 A1    8/2019

OTHER PUBLICATIONS

Farnoud, N. et al., "Ultrasound Backscatter Signal Characterization and Classification Using Autoregressive Modeling and Machine Learning Algorithms," Proceedings of the 25th Annual International Conference of the IEEE EMBS, Sep. 17, 2003, Cancun, Mexico, 4 pages.

*Primary Examiner* — Soo Shin
(74) *Attorney, Agent, or Firm* — McCoy Russell LLP

(57) ABSTRACT

Various methods and systems are provided for thermal monitoring of tissue with an ultrasound imaging system. In one embodiment, a method comprises acquiring, via an ultrasound probe, an ultrasound image, selecting at least one region of interest in the ultrasound image, extracting features from the at least one region of interest, classifying a thermal state of tissue in the at least one region of interest based on the features, and outputting, via a display device, the thermal state of the tissue. In this way, ultrasound imaging may be used for real-time thermal monitoring of tissue during an ablation procedure, thereby improving the accuracy and efficacy of the ablation procedure.

18 Claims, 18 Drawing Sheets

(56) References Cited

U.S. PATENT DOCUMENTS

| | | | |
|---|---|---|---|
| 8,603,015 B2 | 12/2013 | Rosemberg et al. | |
| 8,852,103 B2 * | 10/2014 | Rothberg | A61B 8/4245 |
| | | | 600/438 |
| 8,864,669 B2 * | 10/2014 | Behar | A61B 8/00 |
| | | | 600/438 |
| 8,968,201 B2 * | 3/2015 | Hill | A61B 8/5223 |
| | | | 600/438 |
| 2007/0106157 A1 * | 5/2007 | Kaczkowski | A61B 8/5223 |
| | | | 600/438 |
| 2009/0105588 A1 * | 4/2009 | Emelianov | A61B 18/20 |
| | | | 600/438 |
| 2018/0310987 A1 * | 11/2018 | Altmann | A61B 18/1206 |
| 2022/0007946 A1 * | 1/2022 | Ziegle | G06T 7/0014 |
| 2022/0015742 A1 * | 1/2022 | Grover | A61L 31/045 |

* cited by examiner

METHODS AND SYSTEMS FOR THERMAL MONITORING OF TISSUE WITH AN ULTRASOUND IMAGING SYSTEM

FIELD

Embodiments of the subject matter disclosed herein relate to ultrasound imaging, and more specifically to thermal monitoring via ultrasound imaging.

BACKGROUND

Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body.

In some instances, the location of a tumor may be inaccessible for such an invasive procedure. In such instances, minimal invasive thermal therapy is a potential treatment for solid internal malignancies. For example, radiofrequency ablation (RFA) may be used to destroy cancerous or pathological tissue by heat through percutaneous application of high-frequency energy applied directly to the tumor. More specifically, by creating an alternating electric field within the tissue, ions are agitated in the region neighboring the electric field source (typically an electrode positioned in the region via an RFA needle), thereby increasing the temperature within the region which results in the destruction or ablation of the pathological tissue. RFA is a predominant treatment for hepatocellular carcinoma (HCC), one of the most common types of primary liver cancer in adults, especially when the HCC is non-resectable.

BRIEF DESCRIPTION

In one embodiment, a method comprises acquiring, via an ultrasound probe, an ultrasound image, selecting at least one region of interest in the ultrasound image, extracting features from the at least one region of interest, classifying a thermal state of tissue in the at least one region of interest based on the features, and outputting, via a display device, the thermal state of the tissue. In this way, ultrasound imaging may be used for real-time thermal monitoring of tissue during an ablation procedure, thereby improving the accuracy and efficacy of the ablation procedure.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
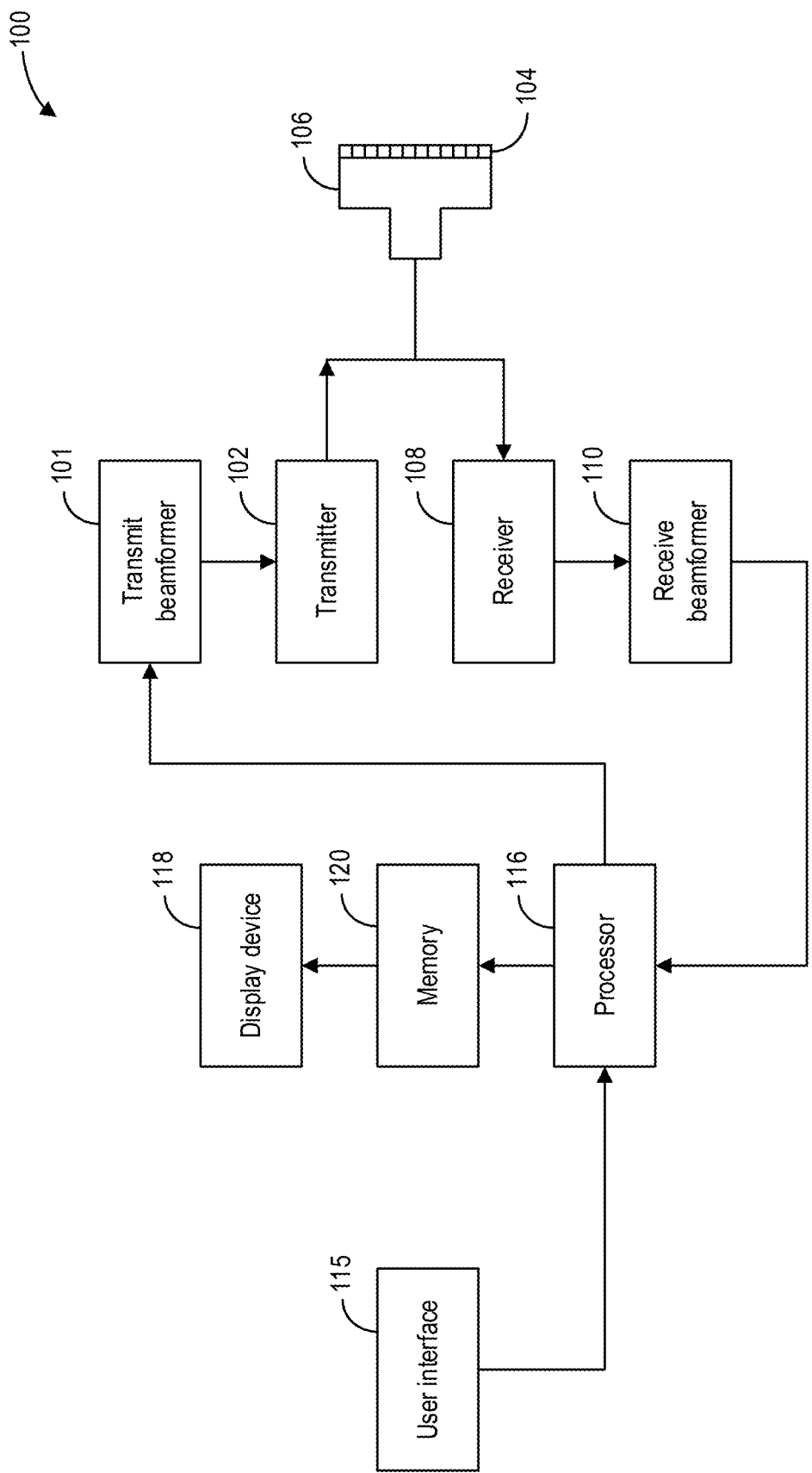
FIG. 1 shows a block diagram illustrating an example ultrasound imaging system, according to an embodiment.
Figure 4:
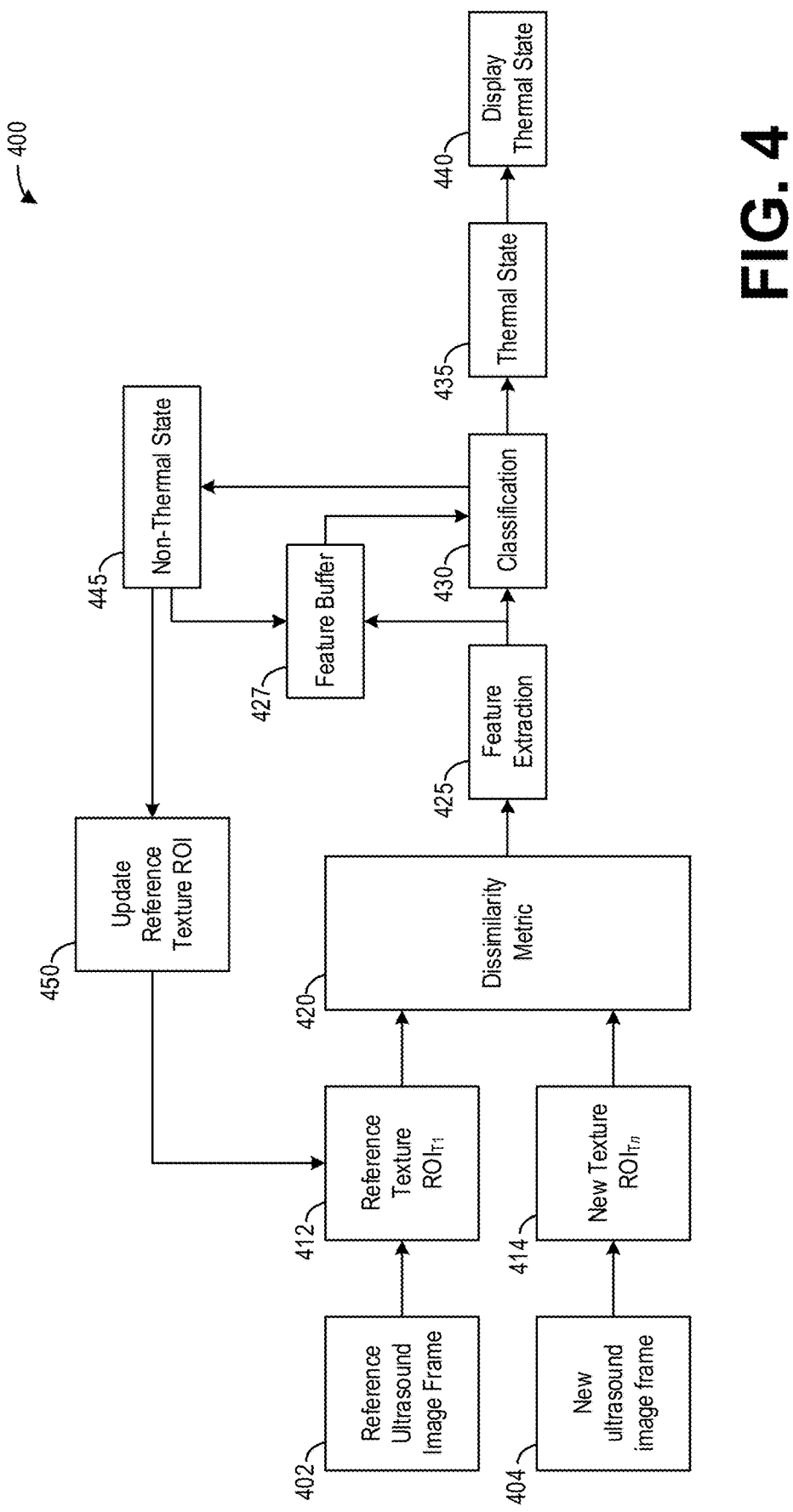
FIG. 4 shows a block diagram illustrating an example method for thermal monitoring with an ultrasound imaging system, according to an embodiment.
Figure 5:
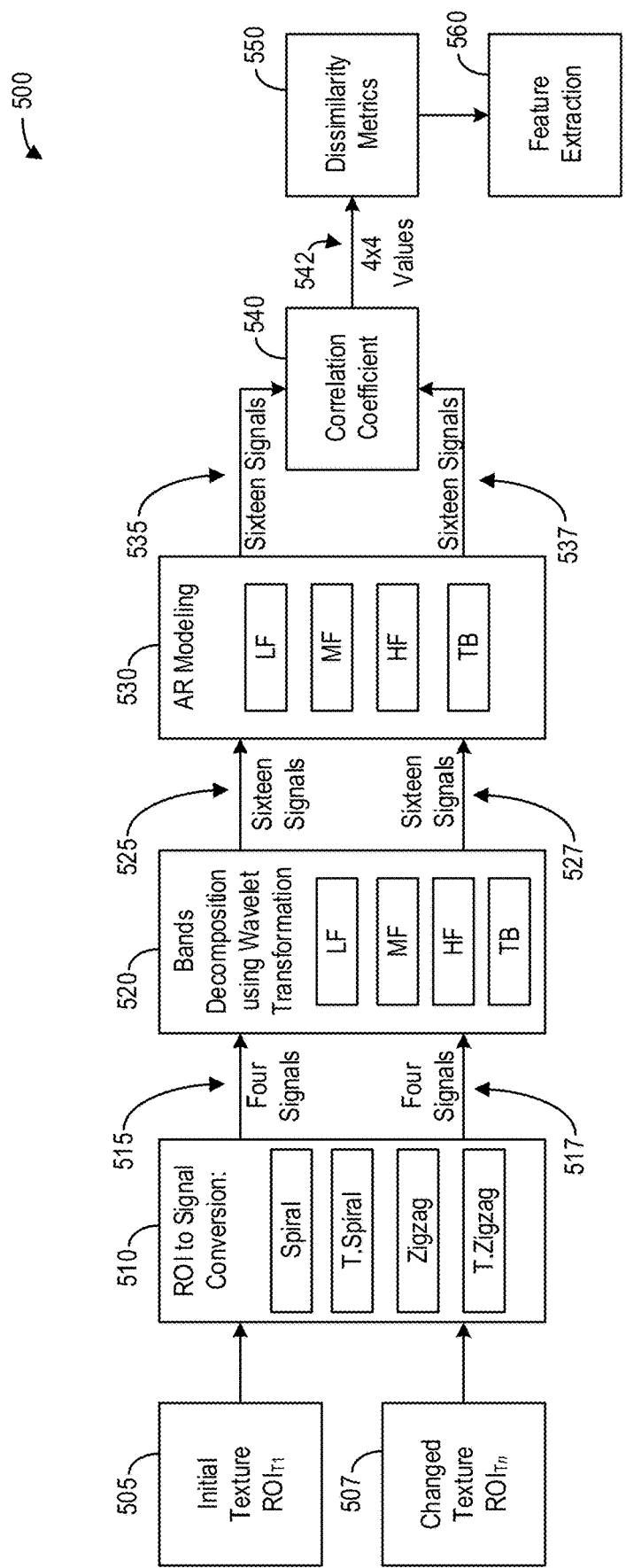
FIG. 5 shows a block diagram illustrating an example method for extracting texture features from regions of interest in an ultrasound image, according to an embodiment.
Figure 6:
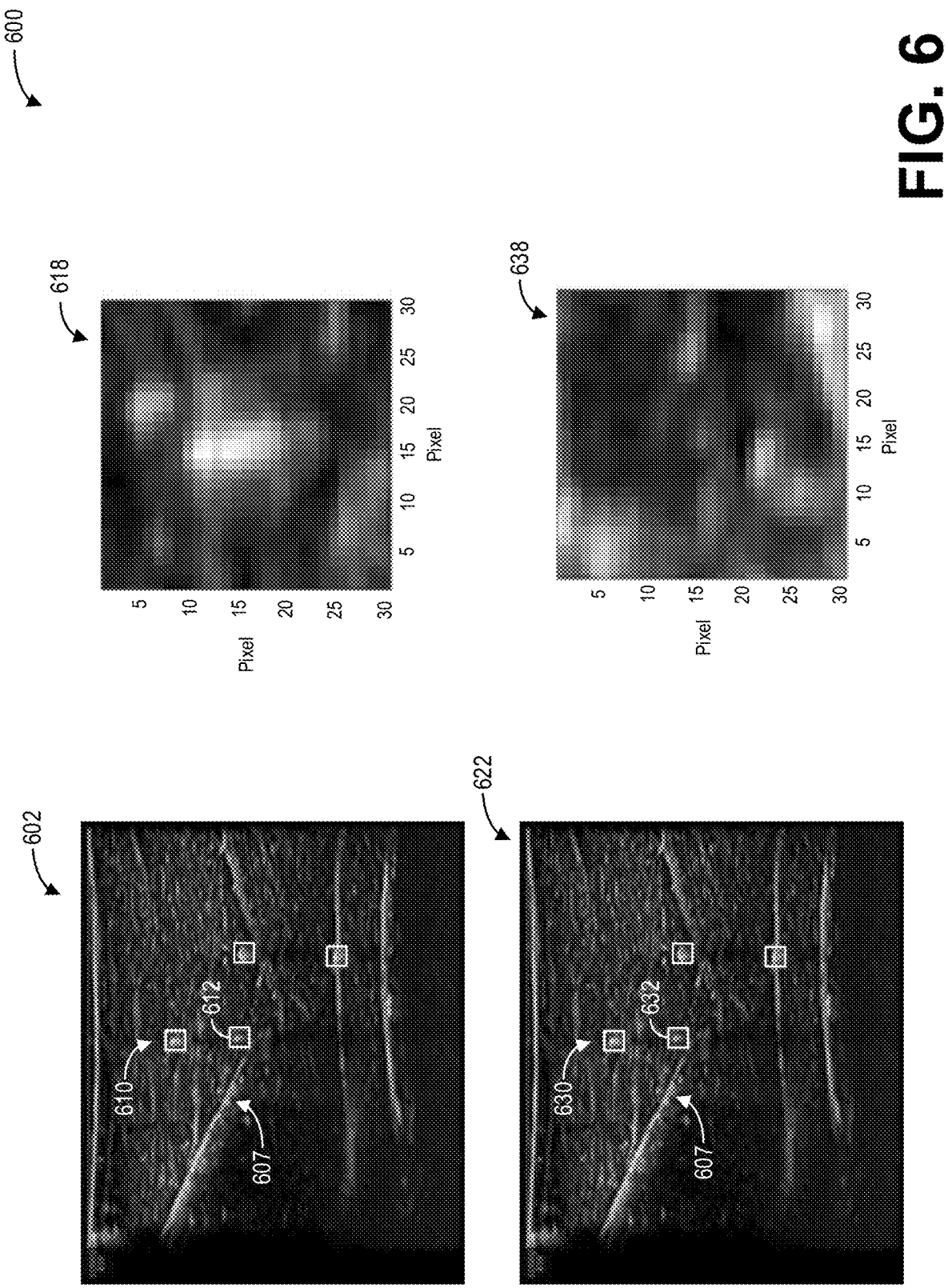
FIG. 6 shows a set of images depicting regions of interest for ultrasound images of tissue at different thermal states, according to an embodiment.
Figure 7:
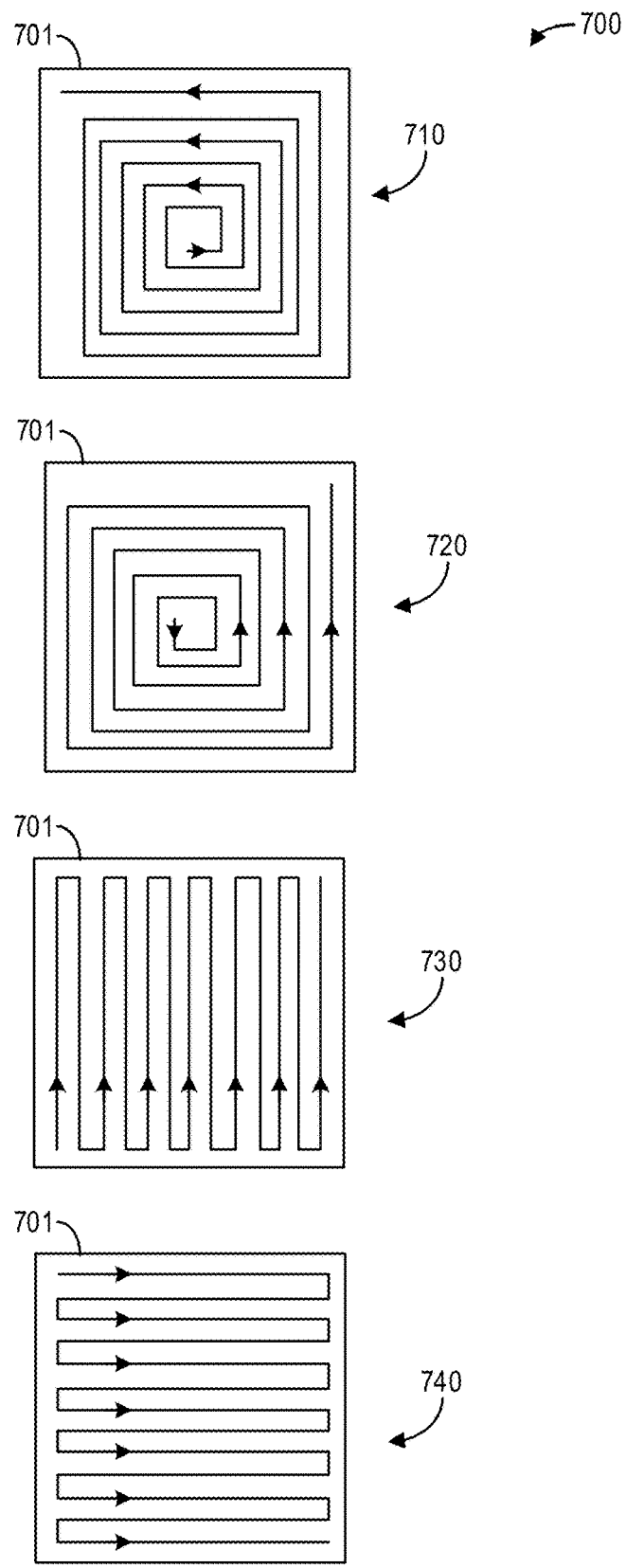
FIG. 7 shows a set of diagrams depicting example pixel trajectories for image-to-signal conversion, according to an embodiment.
Figure 8:
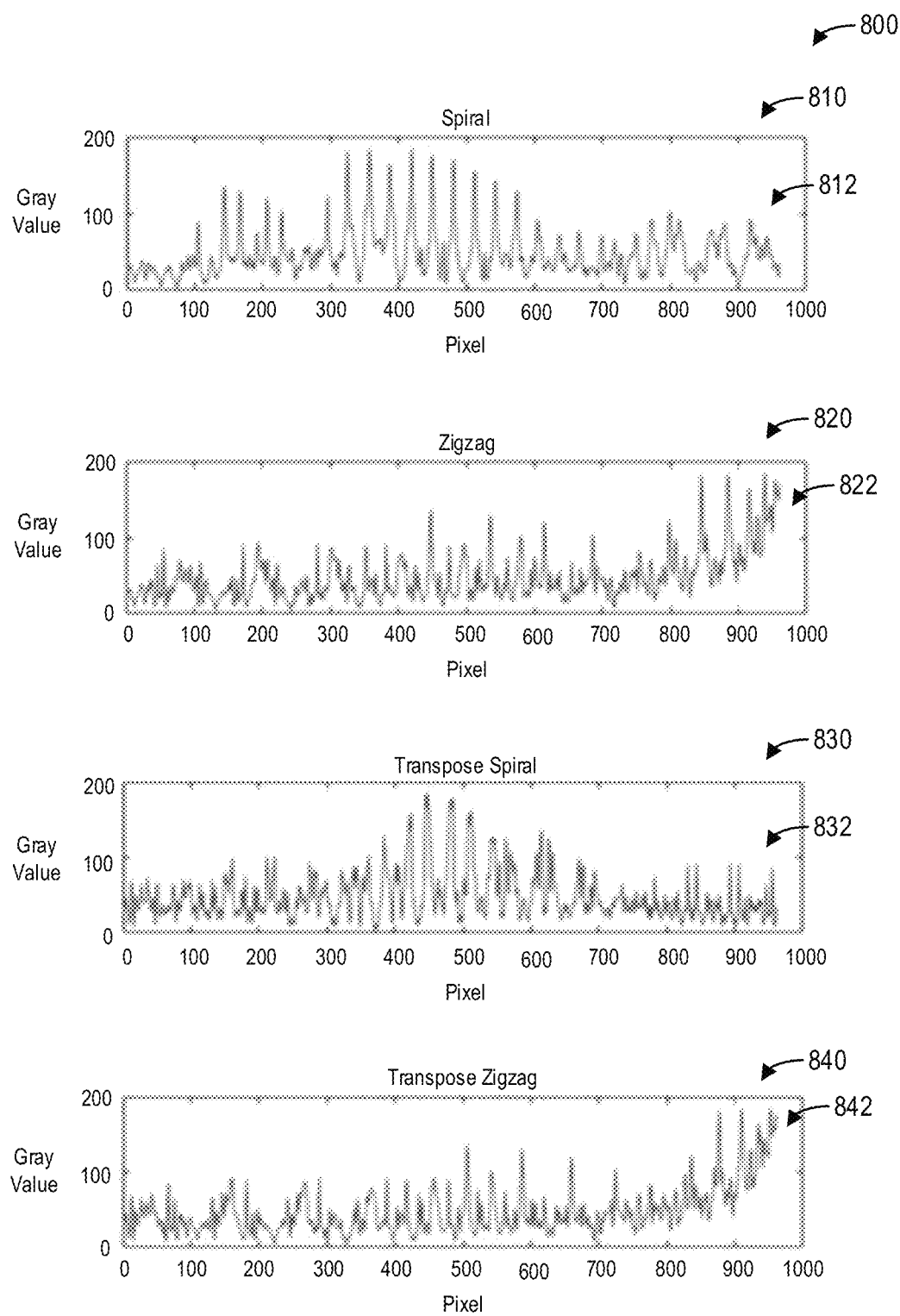
FIG. 8 shows a set of graphs illustrating example signals constructed from a single region of interest with different pixel trajectories for a first thermal state, according to an embodiment.
Figure 9:
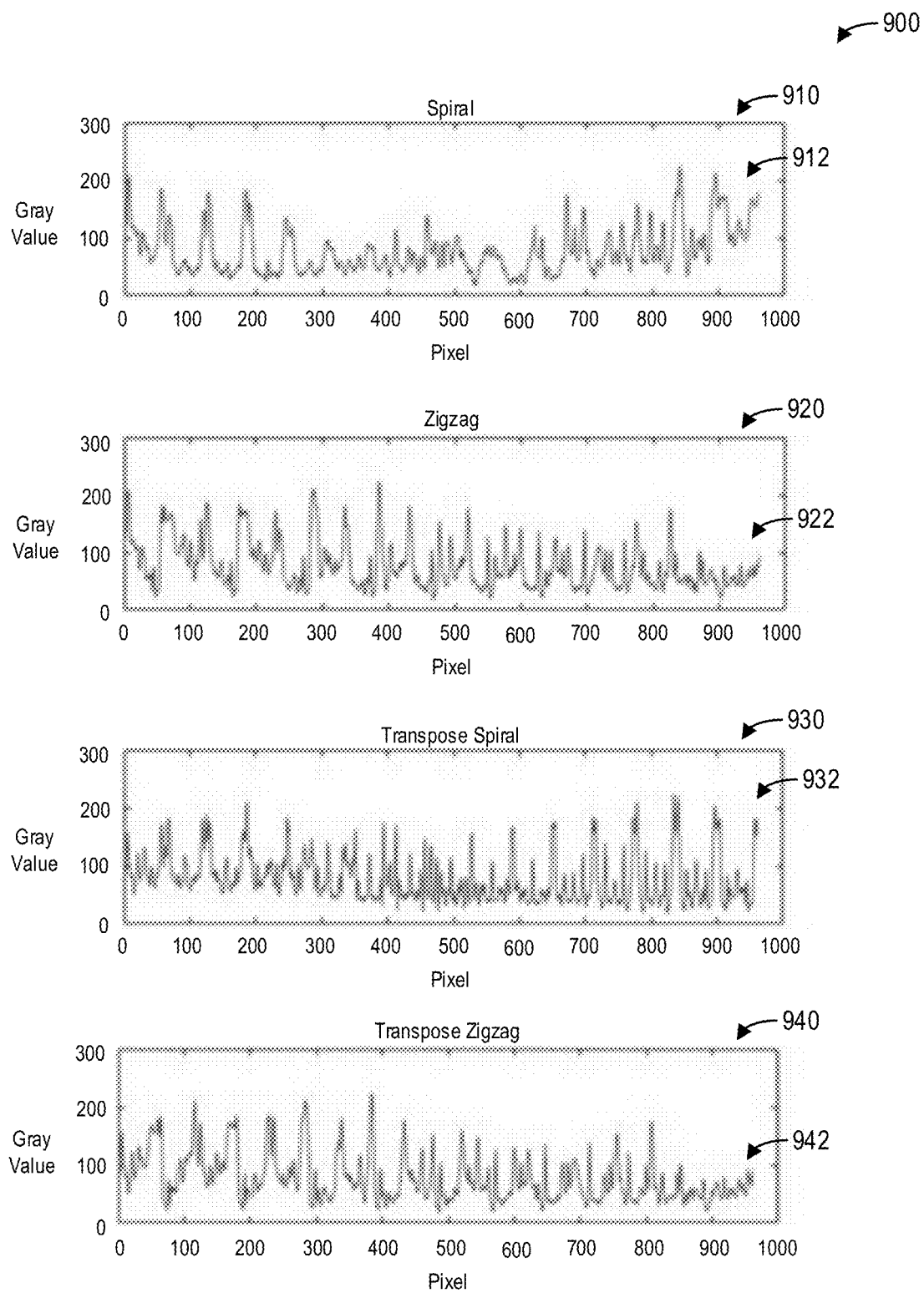
FIG. 9 shows a set of graphs illustrating example signals constructed from a single region of interest with different pixel trajectories for a second thermal state, according to an embodiment.
Figure 10:
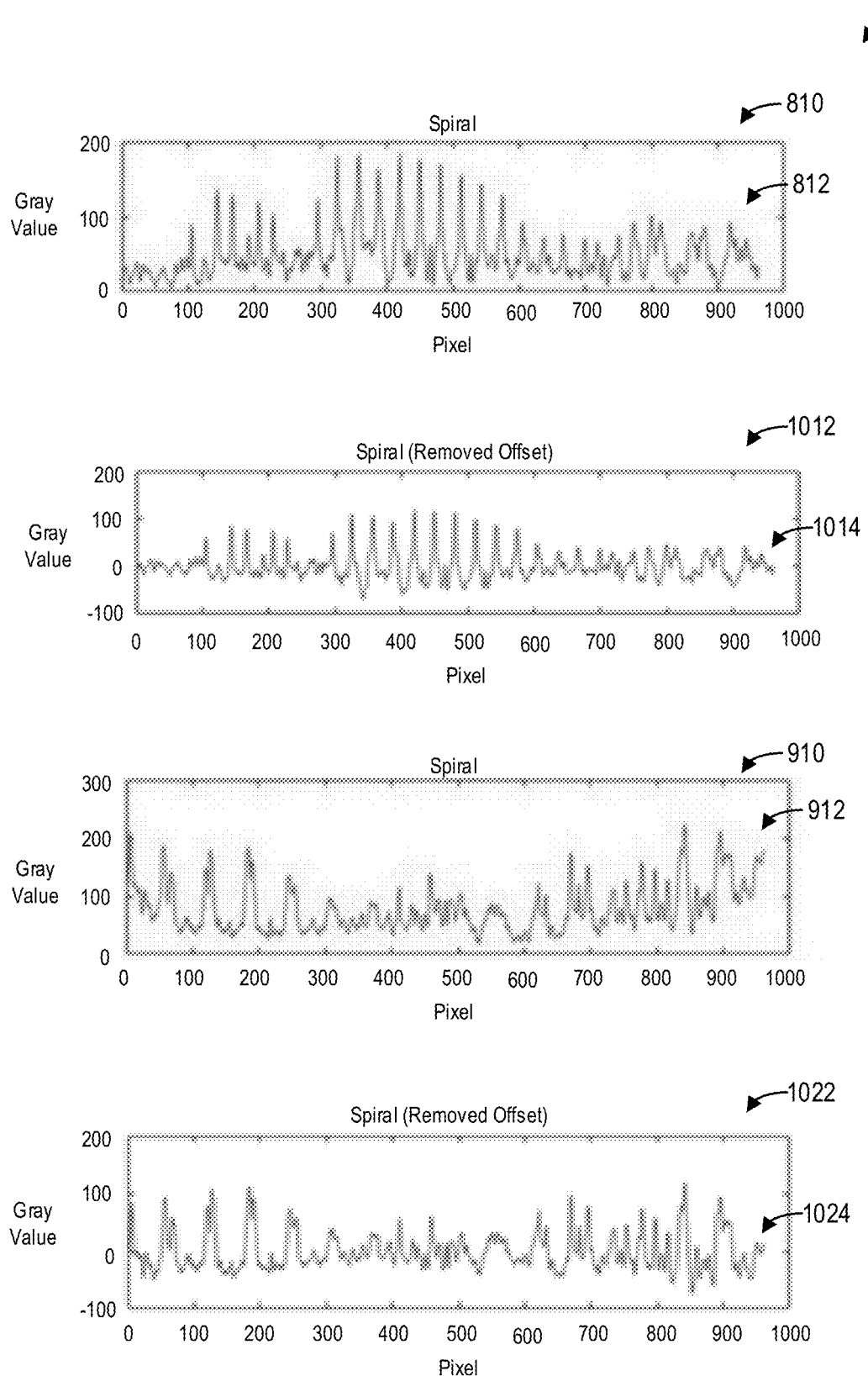
FIG. 10 shows a set of graphs illustrating signal offset correction, according to an embodiment.
Figure 11:
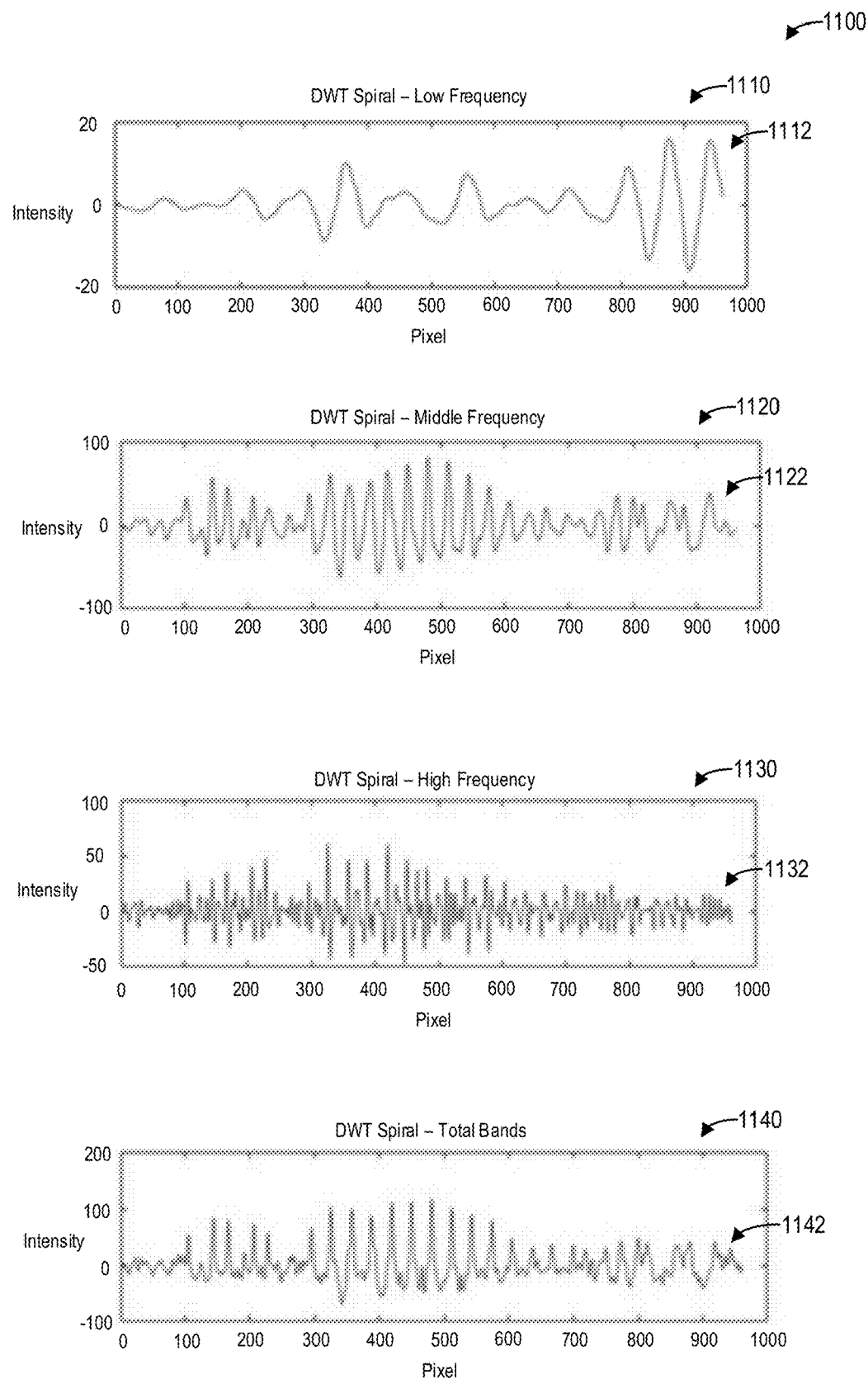
FIG. 11 shows a set of graphs illustrating an example decomposition of texture signals into pseudo-frequency bands for a first thermal state, according to an embodiment.
Figure 12:
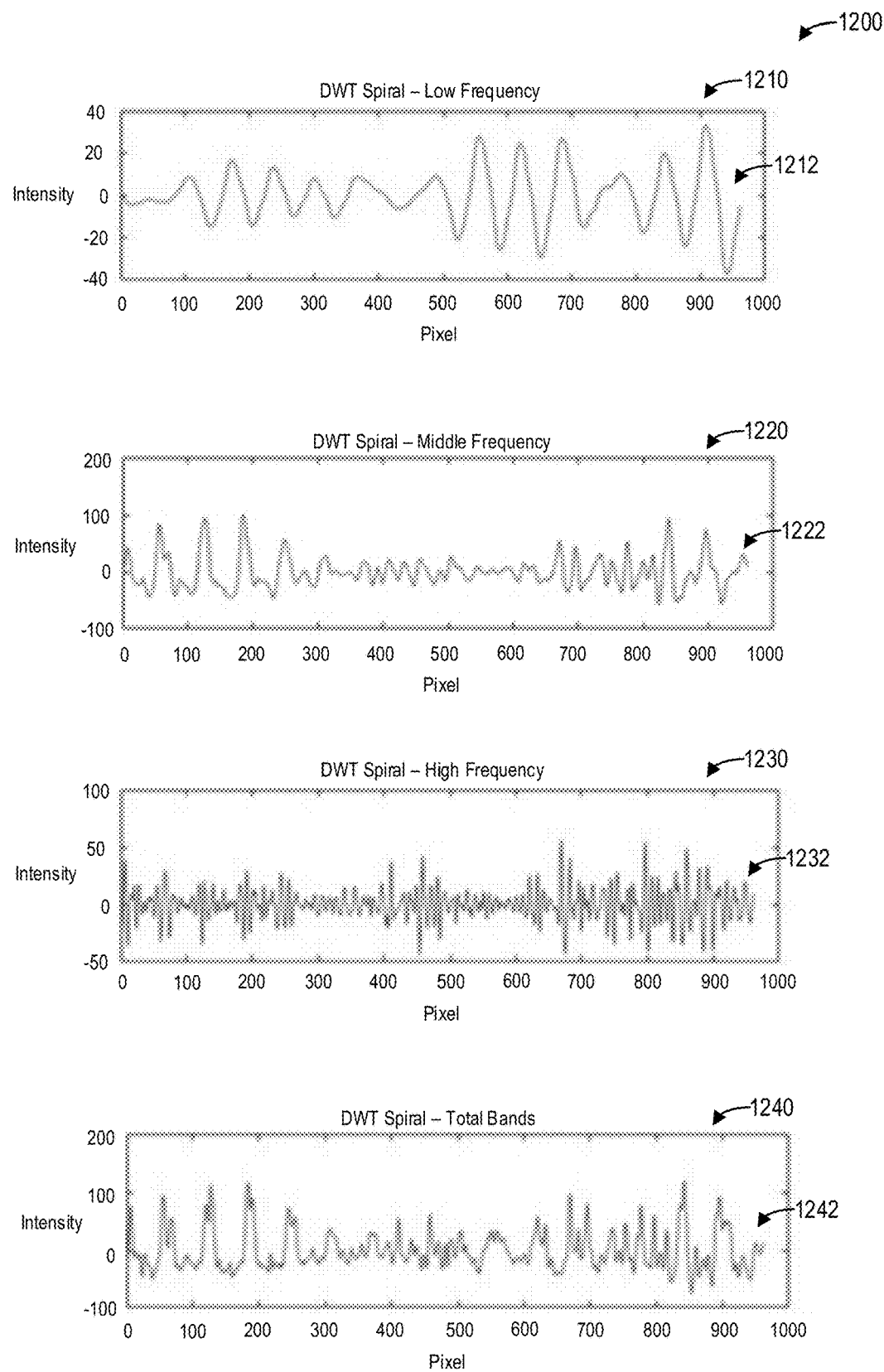
FIG. 12 shows a set of graphs illustrating an example decomposition of texture signals into pseudo-frequency bands for a second thermal state, according to an embodiment.
Figure 13:
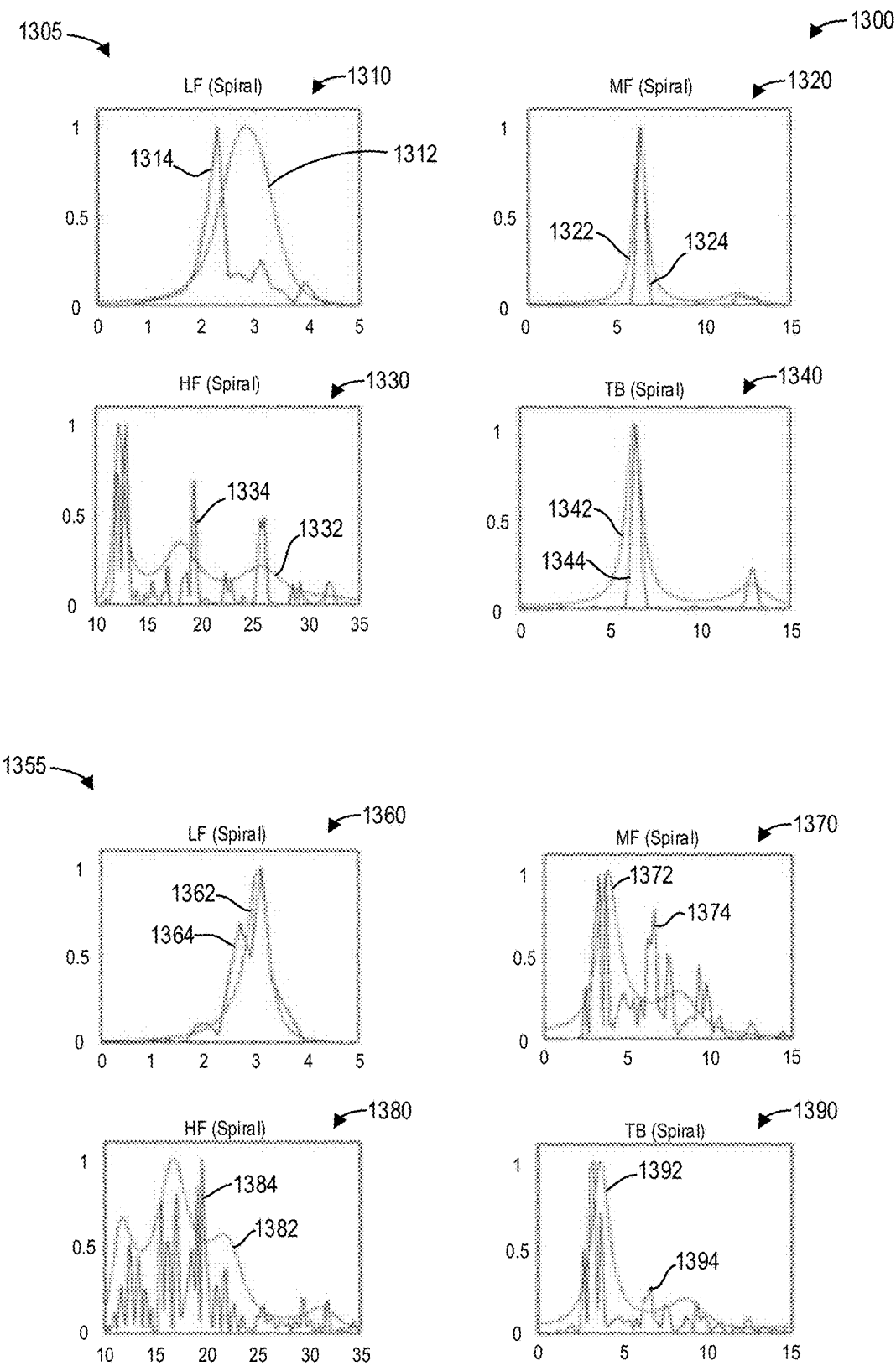
FIG. 13 shows a set of graphs illustrating example power spectral density estimates obtained through autoregressive modeling of decomposed texture signals, according to an embodiment.
Figure 14:
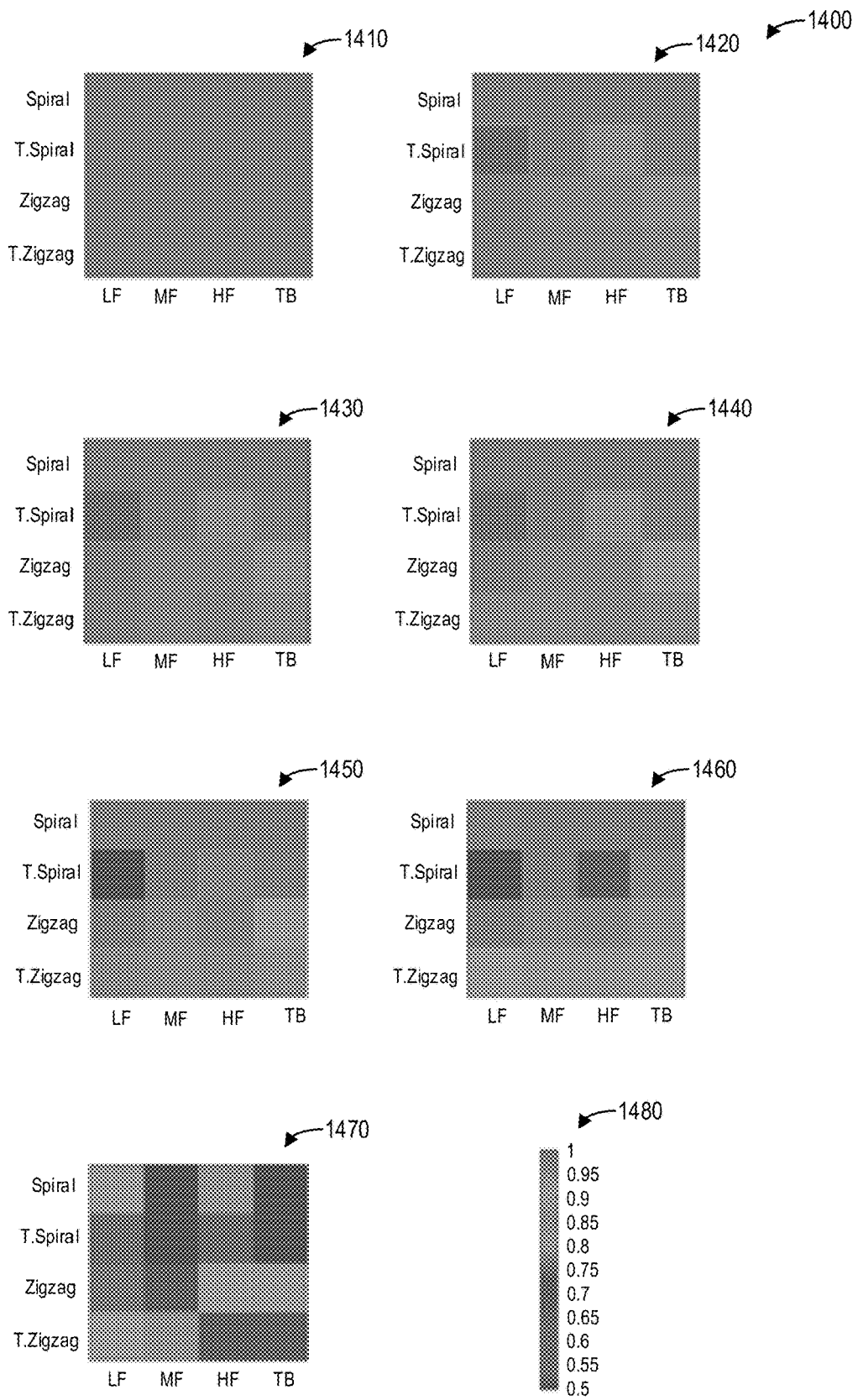
FIG. 14 shows a set of example correlation coefficient maps computed for a plurality of thermal states, according to an embodiment.
Figure 15:
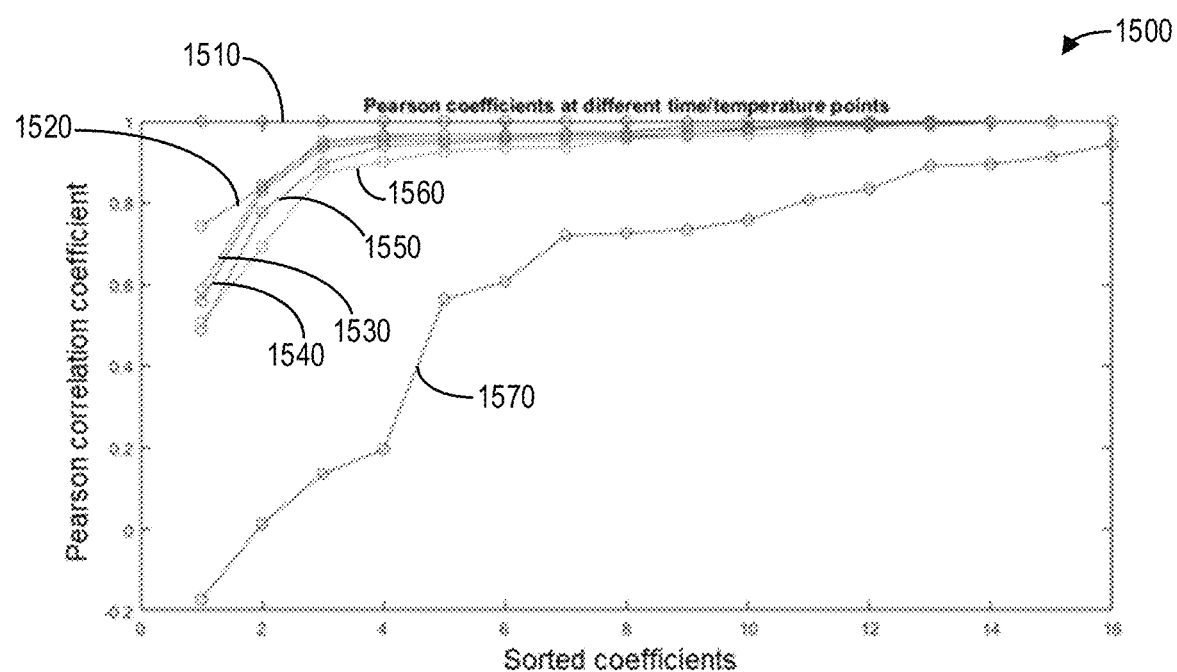
FIG. 15 shows a graph illustrating example dissimilarity metrics of sorted correlation coefficients for different thermal states, according to an embodiment.
Figure 16:
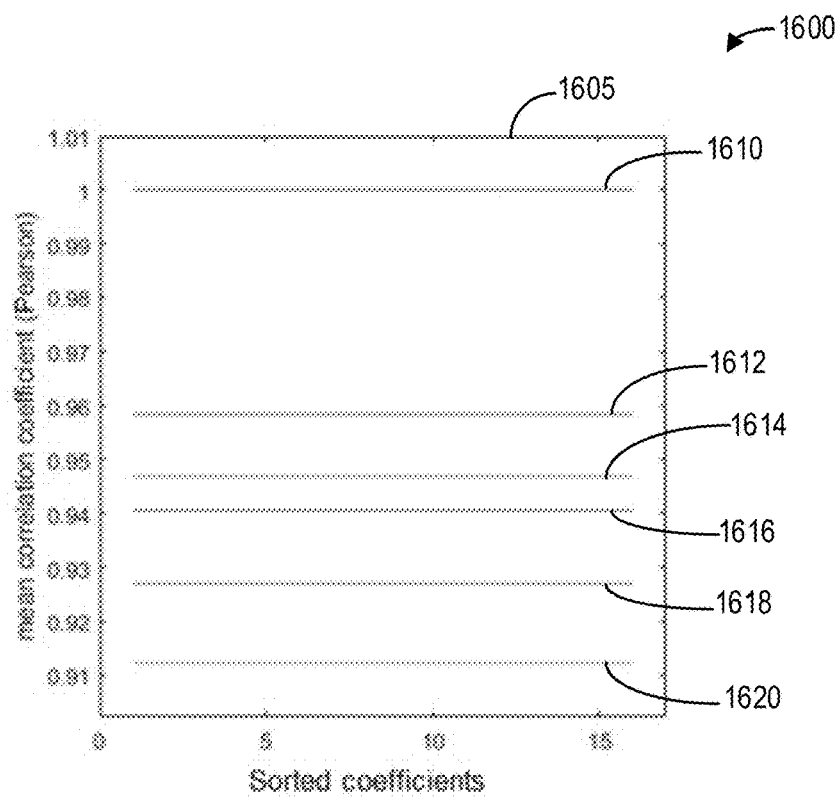
FIG. 16 shows a set of graphs illustrating a first example feature extracted from the dissimilarity metrics for different thermal states, according to an embodiment.
Figure 16:
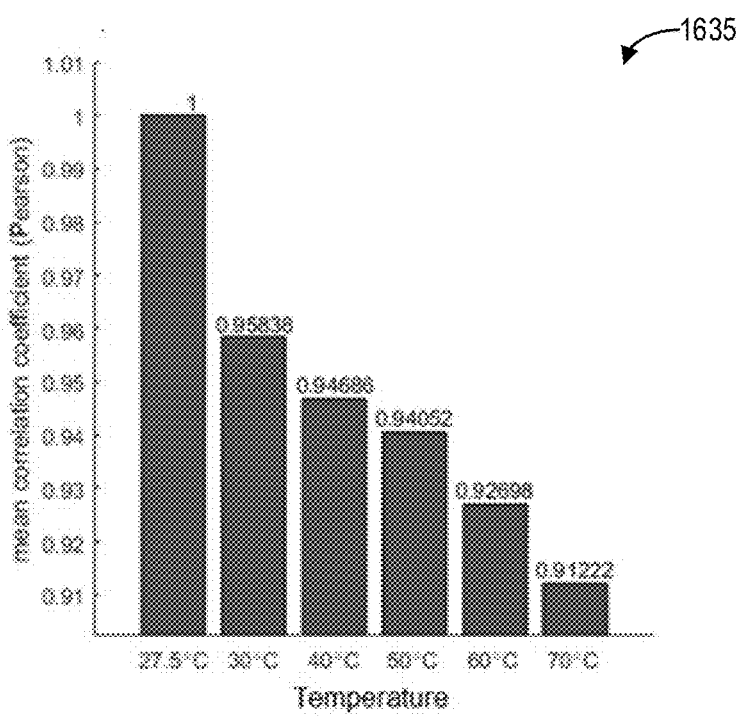
Figure 17:
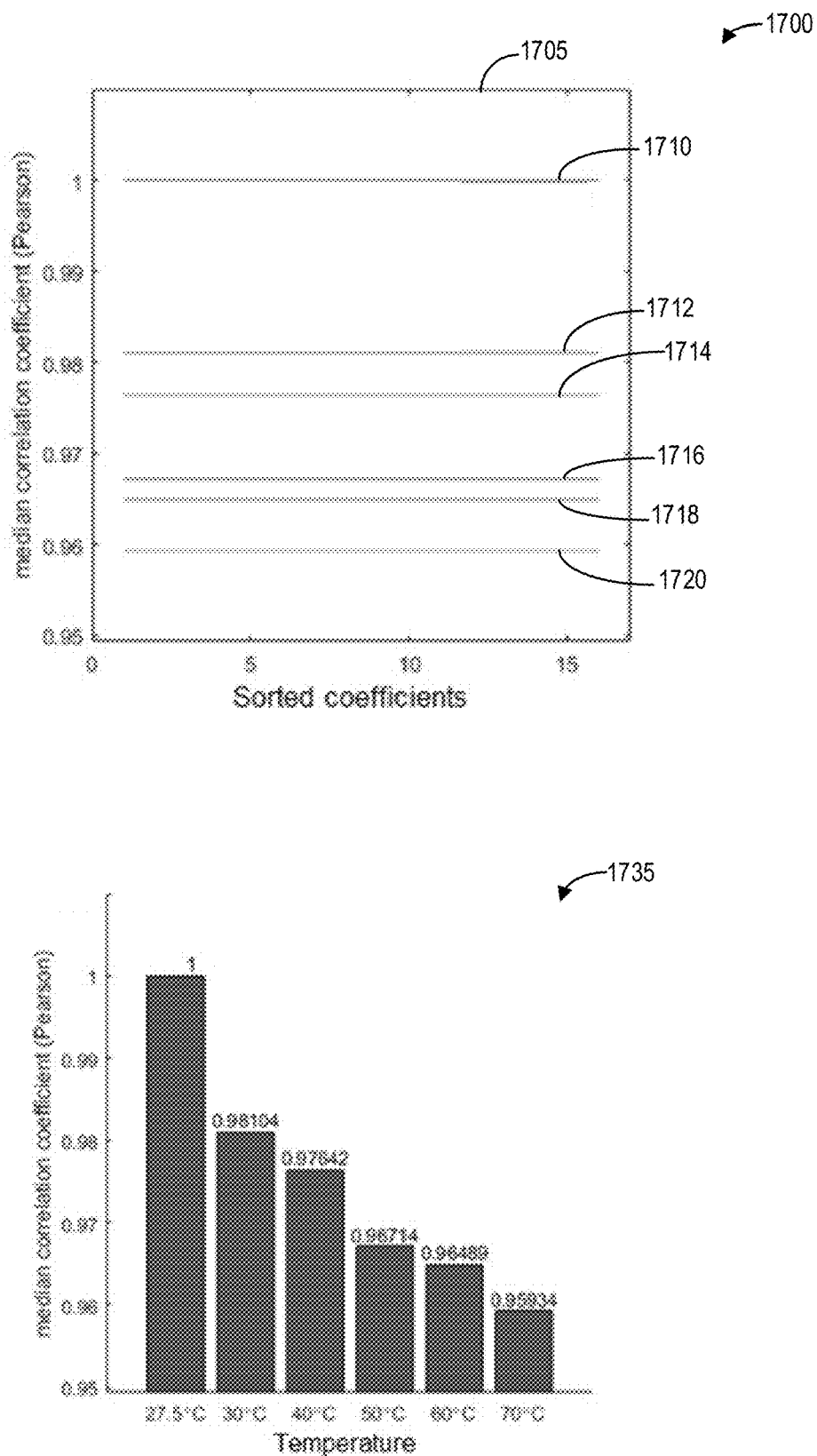
FIG. 17 shows a set of graphs illustrating a second example feature extracted from the dissimilarity metrics for different thermal states, according to an embodiment.
Figure 18:
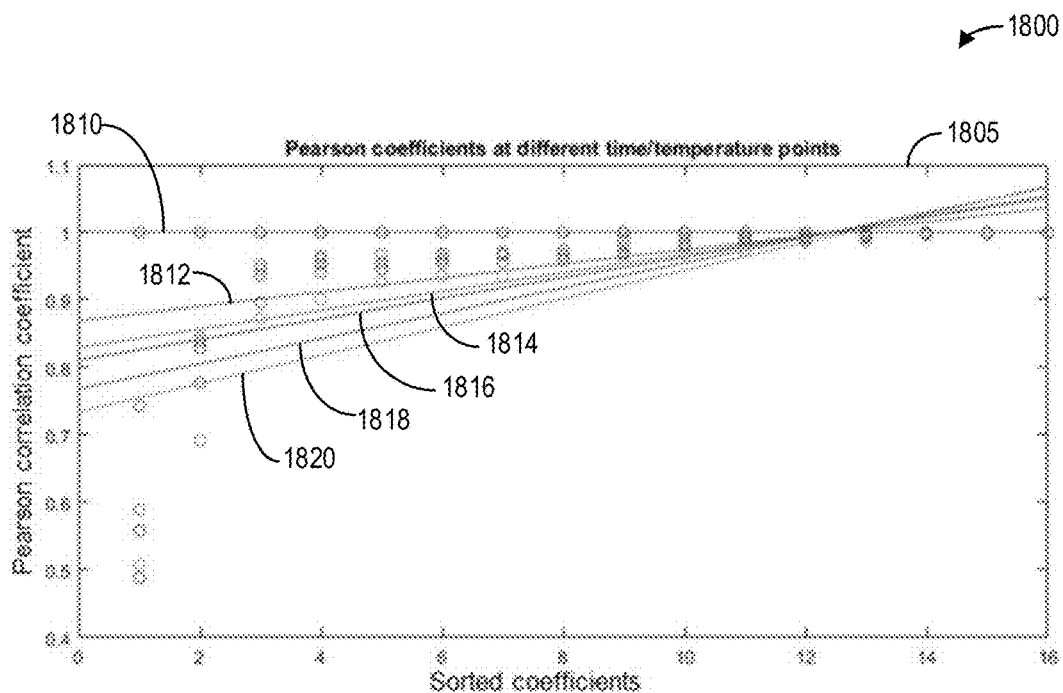
FIG. 18 shows a set of graphs illustrating a third example feature and a fourth example feature extracted from the dissimilarity metrics of the sorted correlation coefficients for different thermal states, according to an embodiment.
Figure 18:
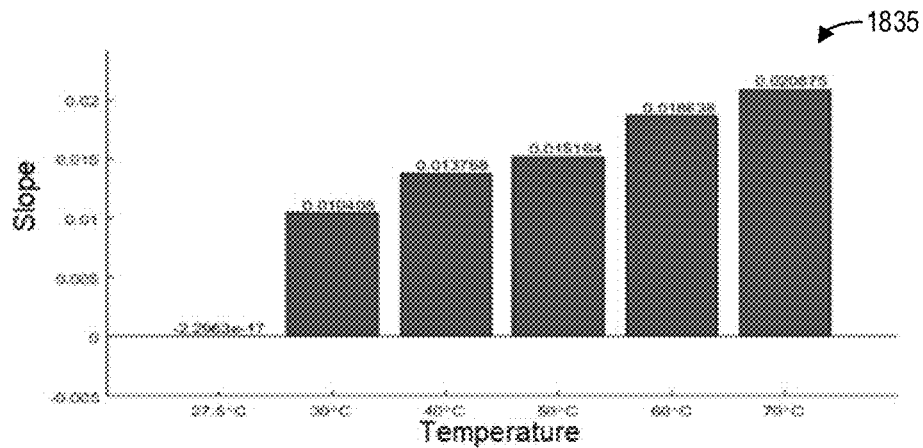
Figure 18:
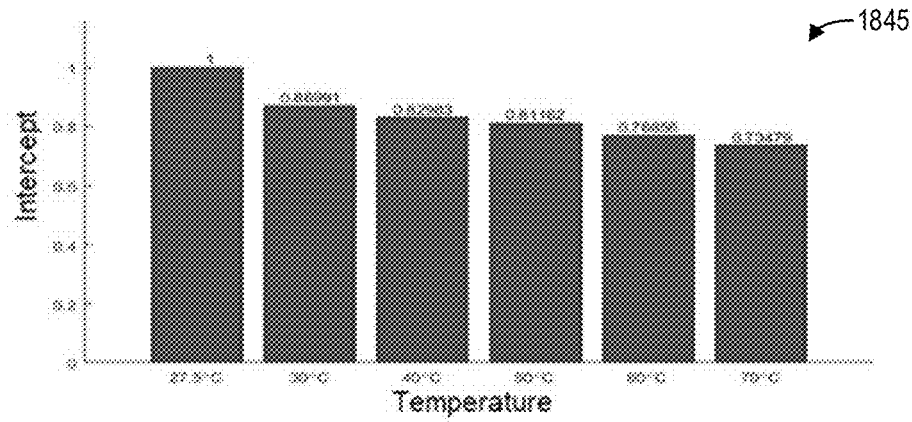

The following description relates to various embodiments of ultrasound imaging. In particular, methods and systems for thermal monitoring of tissue with an ultrasound imaging system are provided. An example of an ultrasound imaging system that may be used to acquire images and perform thermal monitoring in accordance with the present techniques is shown in FIG. 1. As discussed hereinabove, radiofrequency ablation (RFA) is a predominantly applied treatment method for HCC. Observation of the ablation progression (i.e., monitoring and determining the temperature range of tissue) is a major problem during such thermal procedures. Achieving a temperature above 60° C. ensures that cells in pathological tissues are successfully and irreversibly destroyed. Thermal monitoring is therefore useful for indicating whether the ablation temperature has been reached in a certain segment. Presently, magnetic resonance imaging (MRI) is the gold standard for real-time and non-invasive temperature monitoring during thermal ablation. However, the need for a dedicated MRI-compatible ablation system, high costs for equipment and for MRI time, limited space in the MRI bore, and low availability are major disadvantages for using MRI for thermal monitoring. An ultrasound imaging system such as the ultrasound imaging system depicted in FIG. 1, in contrast, is a portable, low-cost imaging modality and is widely accessible. Such a system may be used for needle guidance in RFA, for example, but previous systems are unable to measure and display tissue temperatures during the RFA procedure. A method for thermal monitoring with an ultrasound imaging system, such as the method depicted in FIG. 2, includes extracting features from regions of interest (ROIs) in ultrasound images, and evaluating the state of tissue based on the extracted features. For example, one or more machine learning algorithms may be trained to classify the temperature of tissue depicted in the ROIs based on the extracted features. A method for extracting features, such as the method depicted in FIG. 3, includes converting the ROIs from two-dimensional images to one-dimensional signals, decomposing each signal into multiple frequency bands, generating an estimate for each decomposed signal with an autoregressive (AR) model, measuring correlations for estimates in a same frequency band, determining measures of dissimilarity based on the correlations, and extracting the features from these measures of dissimilarity. The method for extracting the features, as depicted in FIGS. 4 and 5, includes comparing the changed texture of an ROI (e.g., due to heating of the tissue) to an initial texture of the ROI (e.g., the state of the tissue at the beginning of an ablation procedure), for example as depicted in FIG. 6. The features thus comprise quantitative measures of the dissimilarity between image textures caused by heat, which may thus be correlated (e.g., by effective training of one or more machine learning algorithms) to relative temperature increase of the tissue. Such features may provide more precision for classifying the thermal state of tissue than directly evaluating the image texture of the tissue. In order to derive the features from an image of the tissue, the image may be converted into a plurality of signals by using a respective plurality of pixel-traversing trajectories, as depicted in FIG. 7. The resulting signals for an initial texture, as depicted in FIG. 8, as well as a changed texture, as depicted in FIG. 9, exhibit distinctive signal dynamics despite being obtained from a same image. Further, each signal may be decomposed, after performing an offset correction as depicted in FIG. 10, into a plurality of pseudo-frequency bands as depicted in FIGS. 11 and 12. The use of autoregressive modeling of the frequency-based signals yields AR estimates of power spectral density (PSD), for example as depicted in FIG. 13, which as a measure of the power content of the signal versus frequency, provides a robust characterization of the tissue texture. Further, the methods provided herein include calculating correlation coefficients between such AR estimates for initial textures and changed textures, thereby yielding a robust measure of the relative change in tissue texture caused by heat, as depicted by FIG. 14. These measures are then organized into dissimilarity metrics, as depicted in FIG. 15, which provide a suitable representation of the dynamic texture shift for extracting the features mentioned hereinabove. In particular, as depicted in FIGS. 16-18, the features may be derived from the dissimilarity metrics to provide relatively simple quantitative measures of the dissimilarity between tissue textures over time, which in turn allows for robust classification of the thermal state of the tissue as ultrasound images are acquired. In this way, the ultrasound imaging system may rapidly and automatically classify the temperature of tissue by processing ultrasound images as described herein. Further, to simplify the classification, the ultrasound imaging system may classify the state of the tissue texture relative to critical ablation temperatures. Further still, given that different tissue in different patients may achieve ablation at different temperatures, the methods provided herein for classifying the thermal state of tissue may generally distinguish between reversible and irreversible damage to the tissue, thereby personalizing the classification of the tissue texture to the patient rather than on a predetermined critical ablation temperature. In this way, a person performing an ablation procedure may use an ultrasound imaging system for robust, real-time thermal monitoring of tissue to ensure accuracy and efficacy of the ablation procedure.

FIG. 1 shows a schematic diagram of an ultrasound imaging system 100 in accordance with an embodiment of the disclosure. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor 116, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Figure 2:
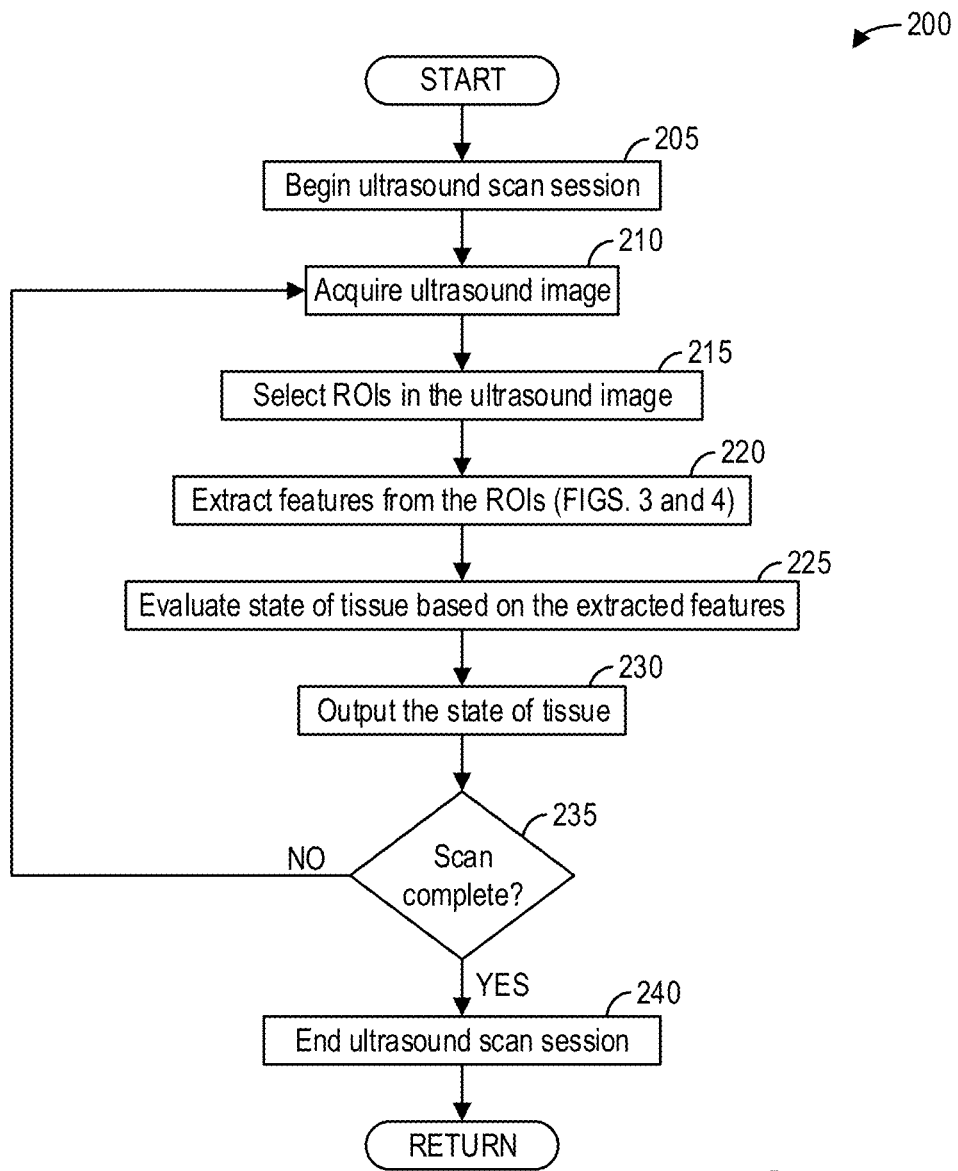
FIG. 2 shows a high-level flow chart illustrating an example method for thermal monitoring during ultrasound imaging, according to an embodiment.

FIG. 2 shows a high-level flow chart illustrating an example method 200 for thermal monitoring during ultrasound imaging, according to an embodiment. In particular, method 200 relates to processing ultrasound images to determine a thermal state of tissue over time, for example during an ablation procedure. Method 200 is described with regard to the system and components of FIG. 1, though it should be appreciated that the method 200 may be implemented with other systems and components without departing from the scope of the present disclosure. Method 200 may be implemented as executable instructions in non-transitory memory, such as the memory 120, that when executed by a processor, such as the processor 116, cause the processor to perform the actions described herein below.

Method 200 begins at 205. At 205, method 200 begins an ultrasound scan session of a patient to provide thermal monitoring of tissue of the patient. The ultrasound scan session may performed during a radiofrequency ablation (RFA) procedure to provide image guidance for a user positioning a radiofrequency ablation needle within tissue. In such an example, the ultrasound scan session may include controlling an ultrasound transducer or ultrasound probe 106, for example, to perform standard B-mode imaging of a region wherein the RFA procedure is being performed. In other examples, the ultrasound scan session may be primarily directed to performing thermal ablation via focused ultrasound. In such examples, the ultrasound scan session may include controlling the ultrasound probe 106 to perform thermal ablation of an ablation region of interest (ROI) via focused ultrasound, and furthermore to acquire B-mode images for thermal monitoring of the tissue. Alternatively, separate ultrasound imaging systems may be used for thermal ablation and thermal monitoring. Further, the ultrasound scan session may be performed to provide thermal monitoring of tissue during ablation of the tissue via other ablation modes, such as microwave therapy, laser ablation, and other heat delivery methods. In yet other examples, the ultrasound scan session may be performed without a concurrent ablation procedure. In any case, the ultrasound scan session initiated at 205 includes acquiring B-mode ultrasound images for thermal monitoring of the tissue.

To that end, at 210, method 200 acquires an ultrasound image. The ultrasound image may comprise a B-mode or grayscale ultrasound image. At 215, method 200 selects regions of interest (ROIs) in the ultrasound image. For example, method 200 selects a plurality of ROIs, each ROI comprising a patch of an image, distributed throughout the ultrasound image. As an illustrative and non-limiting example, each ROI may comprise a 20×20 pixel patch within the ultrasound image. In order to include more information about tissue texture, as another illustrative and non-limiting example, each ROI may comprise a 31×31 pixel patch in the ultrasound image. It should be appreciated that the size of each ROI may be greater or smaller than 31×31 pixels, for example, depending on the resolution of the ultrasound image and the field of view.

At least one ROI may be positioned to align with an ablation ROI. For example, if the ablation method is RFA, at least one ROI of the plurality of ROIs may be positioned at a tip of the RFA needle within the ultrasound image. Additionally or alternatively, at least one ROI of the plurality of ROIs may be centered at a position of an object targeted for ablation, such as a lesion. Remaining ROIs of the plurality of ROIs may be distributed throughout the ultrasound image with a minimum distance from each other, for example to ensure a variety of ROIs with different rates of thermal change. The positions of the ROIs may be selected automatically, manually, or a combination thereof. For example, a user may select a position of an ablation ROI or ablation target, such as a lesion, via the user interface 115 of the ultrasound imaging system 100. Method 200 may then select an ROI for thermal monitoring at the selected position of the ablation target, and automatically select positions of additional ROIs relative to the position of the ROI centered on the ablation target. In other examples, the user may select, via the user interface 115, positions for each ROI for thermal monitoring. In yet other examples, method 200 may automatically select positions for each ROI without user input, for example based on predetermined ROI positions, or by identifying regions of interest via image processing and/or machine learning methods. For example, a convolutional neural network may be trained to automatically determine, with the B-mode ultrasound image as input, a plurality of positions of ROIs for thermal monitoring. In this way, ROIs may be automatically selected, for example, with desirable positions for thermal monitoring (e.g., away from a boundary between bone and tissue, for example, or between organs, which may potentially introduce errors in thermal monitoring).

In some examples, the selected ROIs may be applied consistently to each ultrasound image acquired during the ultrasound scan session to perform thermal monitoring within the selected ROIs. To that end, the positions of the selected ROIs may be fixed or set relative to the anatomical structures depicted within the ultrasound image, such that the thermal monitoring may be consistently applied to each ROI despite slight motion of the ultrasound probe 106 relative to the tissue during the ultrasound scan session or slight motion of the tissue itself (e.g., due to breathing or other patient motion).

After selecting the ROIs for thermal monitoring, method 200 continues to 220. At 220, method 200 extracts features from the ROIs. In particular, method 200 extracts features for thermal monitoring, or thermal features, from the ROIs. Method 200 uses the features or thermal features with machine learning, for example, configured for thermal monitoring of the ROIs. Thus, each feature comprises a measurable property or characteristic of the ROI which may dynamically change responsive to a change in thermal state of the tissue in the ROI. For example, as tissue is heated to a higher temperature, the texture of the tissue as depicted in ultrasound images changes. The features extracted thus quantify the tissue texture in the ultrasound images. A method for extracting features to investigate dynamic changes in tissue texture caused by the heat, such as the methods for extracting features from the ROIs described further herein with regard to FIGS. 3 and 4, includes converting the image data of the ROIs into signals, and extracting features from the signals via a frequency-based autoregressive model approach.

After extracting the thermal features from each ROI, method 200 continues to 225. At 225, method 200 evaluates the state of tissue in the ROIs based on the extracted features. Method 200 may use the extracted features as input to one or more machine learning algorithms configured to evaluate the state of the tissue over time based on the extracted features. As illustrative and non-limiting examples, method 200 may use machine learning algorithm(s) including one or more of a random forest classifier (RFC), a support vector machine (SVM), and an artificial neural network (ANN) to evaluate the state of the tissue in the ROIs based on the extracted features.

Evaluating the state of tissue in the ROIs based on the extracted features may comprise classifying the thermal state of the tissue in each ROI. For example, the one or more machine learning algorithms may be trained to classify the temperature of the tissue in each ROI. The one or more machine learning algorithms may therefore output, based on the extracted features input to the machine learning algorithm(s), a temperature classification of the tissue in each ROI. For example, the temperature classification may comprise a classification of the temperature within predefined temperature bins. For example, the temperature in each ROI may be classified as above or below one or more temperature thresholds. As an illustrative and non-limiting example, the temperature in each ROI may be classified as above or below 60° C., for example, or another temperature threshold. The temperature threshold(s) may be determined based on ablation dynamics, for example, such that the threshold(s) correspond to one or more critical temperatures for ablation, such as a temperature at which tissue is permanently affected or damaged by the ablation procedure. Such a critical temperature may vary for different types of tissue or different types of patients, for example, and so in some examples at least two temperature thresholds may be provided to define an ablation range. For example, ablation may occur between 55° C. and 65° C., and so the temperature in each ROI may be classified as below a first temperature threshold (e.g., 55° C.), above a second temperature threshold (e.g., above 65° C.), or therebetween (e.g., between 55° C. and 65° C.). However, as an ablation procedure may not be conducted for long enough after the tissue reaches the first temperature threshold for the tissue to reach the second temperature threshold, in some examples the one or more machine learning algorithms may only be trained to classify the temperature relative to the first or lower temperature threshold. As another example, the predefined temperature bins may comprise a bin for each temperature degree, such that the temperature of the tissue may be classified more precisely.

Alternatively, the one or more machine learning algorithms may be trained to classify dynamic changes in the texture state. For example, the one or more machine learning algorithms may classify the state of the tissue as reversible (e.g., tissue not yet ablated) or irreversible (e.g., tissue ablated), and additionally may classify the state of the tissue as coagulation. In this way, the machine learning algorithm(s) may identify whether the state of the tissue indicates that ablation is complete, which may occur at different temperatures for different tissues and/or different patients.

After evaluating the state of the tissue in each ROI, method 200 continues to 230. At 230, method 200 outputs the state of the tissue determined at 225. For example, method 200 may display the results of the evaluation at 225 via the display device 118. If the state of tissue is characterized via temperature classifications as described hereinabove, method 200 may display the temperature classification(s) for at least one ROI via the display device 118. The temperature classification(s) may be displayed as text adjacent to the ultrasound image, for example, or superimposed over the ultrasound image at the ROI position, in some examples. Additionally or alternatively, the temperature classification(s) may be displayed graphically relative to the display of the ultrasound image (e.g., as a heat map) to assist the user in visualizing the temperature of the tissue in the ultrasound image. By outputting the state of the tissue in this way, a user of the ultrasound imaging system 100 may understand the state of the tissue in real-time during an ablation procedure. In turn, the user may adjust the ablation procedure (e.g., by ending the procedure or adjusting parameters of the ablation procedure) responsive to the current state of the tissue.

In addition to outputting the state of the tissue to the display device 118 for display to the user of the ultrasound imaging system 100, method 200 may also output the state of the tissue to memory 120 for storage and subsequent review.

After outputting the state of the tissue at 230, method 200 continues to 235. At 235, method 200 determines whether the ultrasound scan session is complete. Method 200 may determine, for example, that the ultrasound scan session is complete relative to receiving an input command from the user, for example via the user interface 115, to end the ultrasound scan session. In the absence of such a command to end the ultrasound scan session, method 200 may presume the scan is not complete. If the ultrasound scan session is not complete ("NO"), method 200 returns to 210. Method 200 may thus continue acquiring ultrasound images, extracting features from ROIs in the acquired ultrasound image, and evaluating the state of tissue based on the extracted features, for each ultrasound image acquired during an ultrasound scan session. It should be appreciated that the ROIs selected in the ultrasound image at 215 may be maintained for subsequent ultrasound images. Further, the features extracted from the ROIs, and thus the state of the tissue, may be determined relative to the initial ultrasound image acquired during the ultrasound scan session.

Finally, referring again to 235, once the scan is complete ("YES"), method 200 continues to 240. At 240, method 200 ends the ultrasound scan session. Method 200 then returns. Thus, a method is provided for real-time thermal monitoring of tissue. The method may be executed for thermal monitoring during an ablation procedure, for example, or for non-invasive thermal monitoring in general of tissue in a patient.

Figure 3:
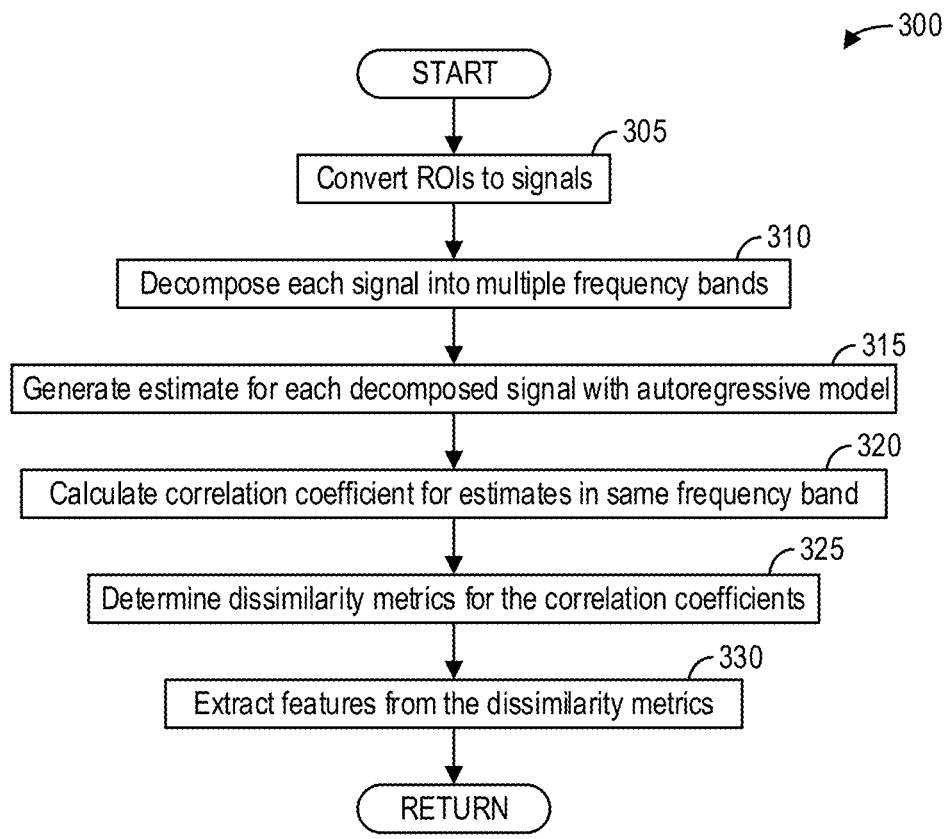
FIG. 3 shows a high-level flow chart illustrating an example method for extracting texture features from regions of interest in an ultrasound image, according to an embodiment.

FIG. 3 shows a high-level flow chart illustrating an example method 300 for extracting texture features from regions of interest in an ultrasound image, according to an embodiment. In particular, method 300 relates to extracting features from ROIs in ultrasound images acquired during an ultrasound scan session, and thus may comprise a subroutine of the method 200 described hereinabove. Method 300 is described with regard to the systems and components of FIG. 1 as well as the method 200 of FIG. 2, though it should be appreciated that the method 300 may be implemented with other systems, components, and methods without departing from the scope of the present disclosure. Method 300 may be implemented as executable instructions in non-transitory memory, such as the memory 120, that when executed by a processor, such as the processor 116, cause the processor to perform the actions described herein below.

Method 300 begins at 305. At 305, method 300 converts the ROIs to signals. In particular, for each ROI, method 300 concatenates all pixel values (e.g., the gray value of each pixel) of the two-dimensional ROI into a single one-dimensional vector. In some examples, method 300 uses a plurality of trajectories for traversing the pixels of each ROI during conversion, such that each ROI is converted into a plurality of signals. For example, method 300 may use a spiral trajectory (e.g., starting from the image center and spiraling outwards), an inverse spiral trajectory (e.g., a transpose trajectory of the spiral trajectory), a zig-zag trajectory (e.g., traversing along columns of the ROI), and a transpose zig-zag trajectory (e.g., traversing along rows of the ROI). Such example trajectories for traversing pixels when converting ROIs to signals are described further herein with regard to FIG. 7.

Thus, method 300 may convert each ROI into four corresponding signals, as an illustrative and non-limiting example. The four signals thus obtained for an ROI represent the tissue texture of the ROI in four different ways. Due to the variety of pixel-traversing trajectories, different dynamics of the signals for a single ROI are observable, and the evolution of such dynamics, even for the same trajectories, over time as the tissue texture changes (e.g., due to the ablation procedure) can be quantified as described further herein.

The signal dynamics are more easily observed in the frequency domain. Therefore, continuing at 310, method 300 decomposes each signal into multiple frequency bands, each representing different dynamics or aspects of the texture. In one example, method 300 decomposes each signal or texture signal using discrete wavelet transform (DWT). The signal trend for each signal affects the singularities on both ends of the wavelet-transformed signal which may cause a negative effect on the frequency band decomposition. Thus, prior to decomposition, method 300 first performs offset removal (i.e., removal of the signal trend) for each signal by calculating a moving average intensity (e.g., gray value) for each signal, and subtracting the moving average intensity from the signal. Example signals with the signal trend or offset removed are described further herein with regard to FIG. 10.

Method 300 decomposes each signal, with offset removed, into a low frequency band (LF), a middle frequency band (MF), a high frequency band (HF), and a total frequency band (TB), using an appropriate scale selection in DWT. As the signals are generated from a spatial series rather than a time series, method 300 uses a pseudo-frequency range in order to apply the wavelet transform to the signals. As an illustrative and non-limiting example, a frequency range from 0 Hz to 100 Hz in the texture signals may be defined and a sampling frequency of 200 Hz may be selected for the wavelet transform. The scale selection may differ for the type of tissue being imaged, as the scales for DWT contain dynamics that may be specific to the type of tissue being imaged. The particular scales to use for DWT may be determined by analyzing spectrograms of ROI data for different types of tissue, for example with a scale of 1 to 10 over a whole ablation sequence, which reveal the frequency-based texture dynamics for the types of tissue. The scales may thus be selected for use with DWT based on the observed frequencies or pseudo-frequencies in each scale and the desired frequency bands. For example, for liver tissue, a scale of 1 may cover a wide range of frequencies with substantial variations, which would be complex for subsequent analysis, and so the scale of 1 may be omitted. Meanwhile, the scales of 2 and 3 may exhibit desirable frequency dynamics to address a high frequency band between, for example, 12 Hz to 35 Hz. Similarly, the scales of 4 and 5 may exhibit desirable frequency dynamics to address a middle frequency band between 3.5 Hz and 11 Hz, while the scales of 6 and 7 may exhibit desirable frequency dynamics to address a low frequency band between 0 Hz and 3.3 Hz. Scales higher than 7 may be neglected or omitted due to either low frequency information or no observable frequency observations. Further, a total frequency band may be chosen by the combination of all selected scales from 2 to 7.

Thus, method 300 uses a discrete wavelet transform, with suitable scale parameters selected for the tissue being imaged, to decompose each signal into four narrow-band signals. It should be appreciated that frequency decomposition methods other than DWT may be used without departing from the scope of the present disclosure. As discussed earlier, four texture signals are obtained for each ROI in the image. After DWT, wherein each texture signal is decomposed into four signals, there are sixteen signals for each ROI in the image.

Continuing at 315, method 300 generates an estimate for each decomposed signal with an autoregressive model. As an illustrative and non-limiting example, method 300 models the sixteen narrow-band texture signals using a parametrical autoregressive (AR) model with a Yule-Walker method. In particular, method 300 models the periodogram for each narrow-band signal by calculating a power spectral density (PSD) from a corresponding estimated AR parameter. The order of the AR model is set individually for each narrow-band signal so that the modeled PSD (i.e., the PSD calculated from the corresponding estimated AR parameter) for a given narrow-band texture signal best matches the periodogram estimated directly from the narrow-band texture signal. As an illustrative and non-limiting example, the AR order for may comprise 35 for the LF signal, 25 for the MF signal, 20 for the HF signal, and 30 for the TB signal. The AR order may be predetermined based on studies of sample tissue textures for different tissues, for example, or may be determined dynamically by method 300 during modeling of the narrow-band texture signals.

The resulting sixteen AR PSD estimates represent the tissue texture inside an ROI in a simplified way. Between textures at two different temperatures, frequency shifts in each frequency band are easily observable in the AR PSD estimates, and the change in texture resulting in such frequency shifts are attributable to the heat applied to the tissue during an ablation procedure. Example periodograms and AR PSD estimates are described further herein with regard to FIG. 13.

After generating the estimates for each decomposed signal with the AR model, method 300 continues to 320. At 320, method 300 calculates correlation coefficients for the estimates in the same frequency band and for the same pixel trajectory used for the ROI-to-signal conversion. That is, method 300 calculates correlation coefficients for each estimate with an initial estimate. In particular, method 300 may calculate a Pearson correlation coefficient for a pair of AR PSD estimates of the same frequency band, including a first AR PSD estimate for the frequency band. Thus, for the first ultrasound image acquired, a correlation coefficient for a given frequency band and pixel trajectory is calculated for the first AR PSD estimate with itself, resulting in a correlation coefficient of one due to the exact correlation. The resulting correlation coefficients may be stored in a correlation coefficient map or matrix, for example as described further herein with regard to FIG. 14.

The AR PSD estimates similar to each other result in a higher correlation coefficient, whereas AR PSD estimates that are dissimilar to each other result in a lower correlation coefficient. While initially all AR PSD estimates are similar and thus highly correlated, as the temperature of an ROI increases and the tissue texture changes in response to the increased temperature, dissimilarities begin to emerge in the various frequency bands and conversion types. For example, dissimilarities in AR PSD estimates may begin emerging across narrow-band signals for the transpose spiral signal, while dissimilarities in the narrow bands of the zig-zag and transpose zig-zag signals increase at higher temperatures.

As the dissimilarities in the narrow bands of each conversion method already exhibit certain behaviors as a function of temperature increase, the correlation coefficients may be used in some examples as features for relating texture changes to temperature levels. However, a more robust method may include combining all of the dissimilarities from the correlation coefficient maps or matrices. To that end, continuing at 325, method 300 determines dissimilarity metrics for the correlation coefficients. To determine the dissimilarity metrics for the correlation coefficients, method 300 sorts the correlation coefficients for each ROI and combines the sorted coefficients into a dissimilarity vector comprising the dissimilarity metric. As an example, for the first ultrasound image acquired, the dissimilarity vector or dissimilarity metric comprises a straight line with all values equal to one, as the correlation coefficients indicate the exact correlation of the AR PSD estimates with themselves. Over time, as the temperature increases and various correlation coefficients evolve away from one (i.e., as the AR PSD estimates become more dissimilar in certain frequency bands and conversion types), the dissimilarity vector exhibits a curvature indicating the increasing dissimilarity. Example dissimilarity vectors are described further herein with regard to FIG. 15.

As the dissimilarity metrics are easily distinguishable over time and temperature, the dissimilarity metrics may be easily described with certain features. Thus, at 330, method 300 extracts features from the dissimilarity metrics. As illustrative and non-limiting examples, method 300 calculates a plurality of features for each dissimilarity metric. The features include a mean value and a median value of the dissimilarity metric. Both the mean value and the median value of the dissimilarity metrics decrease with an increase of temperature. Further, method 300 performs linear regression for each dissimilarity metric, and determines the resulting slope and intercept for the linear regression. The features may thus include the slope and intercept for the linear regression. As temperature increases, the slope increases and the intercept decreases. Thus, method 300 extracts features for each dissimilarity metric, including the median value of the dissimilarity metric, the mean value of the dissimilarity metric, the slope of linear regression for the dissimilarity metric, and the intercept of linear regression for the dissimilarity metric. As described hereinabove with regard to FIG. 2, these features may be used to classify temperature ranges for each ROI. Method 300 then returns.

Thus, a method for extracting features from an image for evaluating the thermal state of tissue is provided. The method includes converting an ROI from a two-dimensional image to a one-dimensional signal using a plurality of pixel-traversal trajectories, decomposing each signal into multiple frequency bands, generating an estimate for each decomposed signal with an autoregressive model, calculating correlation coefficients for estimates in the same frequency band and trajectory type, determining dissimilarity metrics for the correlation coefficients, and calculating features from the dissimilarity metrics. It should be appreciated that while the methods described herein relate to selectively processing an ultrasound image to determine the thermal state of tissue depicted in the ultrasound image, the methods may be adapted to raw ultrasound data, such as the RF data acquired via the ultrasound probe 106, rather than an ultrasound image.

To illustrate an example implementation of the method 200, FIG. 4 shows a block diagram illustrating an example method 400 for thermal monitoring of tissue with an ultrasound imaging system. The method 400 may be implemented as executable instructions in the non-transitory memory of an ultrasound imaging system, such as the memory 120 of the ultrasound imaging system 100, and may be executed by a processor of the ultrasound imaging system, such as the processor 116 of the ultrasound imaging system 100, to perform the actions described herein.

Method 400 acquires a reference ultrasound image frame 402, and selects a reference texture ROI ($ROI_{T1}$) 412. The reference ultrasound image frame 402 includes tissue texture structures at an un-ablated state (i.e., before ablation is performed). Method 400 acquires a new ultrasound image frame 404 including the same tissue texture structures as the reference ultrasound image frame 402 but at an ablated state (i.e., during an ablation procedure). Method 400 selects a new texture ROI ($ROIT_{Tn}$) 414 at the same location as the reference texture $ROI_{T1}$ 412. The reference ultrasound image frame 402 and the new ultrasound image frame 404 are acquired in a same image plane with the same anatomical structures.

Method 400 computes a dissimilarity metric 420 comprising a measurement of dissimilarity of the ROIs 412 and 414. Method 400 computes the dissimilarity metric 420 as described further herein below, for example by converting each ROI to one-dimensional signals, performing trend removal of the one-dimensional signals, decomposing the corrected signals into pseudo-frequency bands, modeling specific ranges in the pseudo-frequency bands, calculating correlations between the corresponding models for the different ROIs, and constructing a correlation vector (e.g., the dissimilarity vector or dissimilarity metric described hereinabove) as output. The dissimilarity metric 420 comprises a measure of the dissimilarity between the texture depicted in the ROIs 412 and 414. As the texture in the ROI 412 depicts the tissue in an un-ablated state, while the texture in the ROI 414 depicts the same tissue during an ablation procedure, an increasing dissimilarity indicates a change in thermal state of the tissue in the ROI 414 relative to the tissue in the ROI 412. As described herein, this quantitative measure of dissimilarity may be associated directly with temperature, such that the thermal state of the tissue in the ROI 414 may be robustly classified. Further, if the dissimilarity metric 420 indicates a similarity rather than a dissimilarity between the ROIs 412 and 414, then method 400 may either determine that the thermal state of the tissue has not changed. That is, a similarity indicates that heat is not being applied to the tissue.

Referring again to FIG. 4, after calculating the dissimilarity metric 420, method 400 then performs feature extraction 425 from the correlation vector, for example by extracting features out of the correlation vector including but not limited to one or more of mean correlation, median correlation, slope and intercept of the linear regression of the correlation vector, energy, energy difference and ratio to a first correlation vector, and so on. The extracted features from the feature extraction 425 are stored in a feature buffer 427. Further, the extracted features from the feature extraction 430 are used as inputs for classification 430 of the new texture $ROI_{Tn}$ 414. In particular, the classification 430 uses the characteristics of the extracted features to classify a thermal state 435 of the new texture $ROI_{Tn}$ 414. The thermal state 435 thus comprises a value assigned to the new texture $ROI_{Tn}$ 414 that represents the class of the thermal state of the tissue depicted in the new texture $ROI_{Tn}$ 414. Method 400 displays the thermal state 435 at 440. For example, method 400 may transform the assigned value of the thermal state 435 for the new texture $ROI_{Tn}$ 414 into a color and augment the corresponding ROI 414 in the new ultrasound image frame 404 with the color.

Classification 430 of the thermal state 435 of the new texture $ROI_{Tn}$ 414 based on the extracted features is more robust and further reduces computational complexity in comparison to a more naïve approach to thermal monitoring, for example based on direct analysis of the textures depicted in the ROIs 412 and 414, or by inputting the ROIs 412 and/or 414 directly into one or more machine learning algorithms. Further, as the dissimilarity metric 420 characterizes the dissimilarity between the ROIs 412 and 414, the features extracted during feature extraction 425 provide an individualized basis for evaluating and classifying the thermal state of tissue.

Further, in some examples, the classification 430 may classify a non-thermal state 445 of the tissue in the new texture $ROI_{Tn}$ 414. For example, the expansion of gas bubbles, tissue shrinking, or tissue expansion may lead to a shift of the tissue texture within the observed ROI. Therefore, the ROI of the reference ultrasound image frame 402 used as the reference texture $ROI_{T1}$ 412 may be updated based on the non-thermal state 445 of the tissue within the new texture $ROI_{Tn}$ 414. Thus, method 400 determines an updated reference texture ROI 450 and replaces the reference texture $ROI_{T1}$ 412 with the updated reference texture ROI 450 for subsequent monitoring.

In order for the classification 430 to classify the non-thermal state 445, features corresponding to a previous ROI or a last known thermal state that are stored in the feature buffer 427 are input to the classification 430, so that the classification 430 may identify the non-thermal state 445 based on a comparison of the previous features from the feature buffer 427 to the current features extracted during feature extraction 425.

Thus, a method is provided for thermal monitoring of tissue with an ultrasound imaging system that includes classifying a thermal state of tissue in an ROI based on a comparison of tissue texture in the ROI with tissue texture from a reference ROI, with updates to the reference ROI over time due to changes in the non-thermal state of the tissue.

To illustrate an example implementation of the method 300, FIG. 5 shows a block diagram illustrating an example method 500 for extracting texture features from regions of interest in an ultrasound image, according to an embodiment. As discussed hereinabove, a method for thermal monitoring of tissue with ultrasound imaging includes comparing textures of a region of interest over time. For example, the method 500 includes comparing an initial texture 505 in an ROI at a first time $T_1$, to a changed texture 507 in the ROI at an nth time $T_n$, where the initial texture 505 in the ROI is depicted in an ultrasound image acquired at the first time $T_1$, while the changed texture 507 in the ROI is depicted in an ultrasound image acquired at the nth time $T_n$. The value n comprises an index number of images in an ultrasound sequence (e.g., such as the ultrasound scan session described hereinabove with regard to FIG. 2), and so the nth time $T_n$ corresponds to the time when the nth ultrasound image is acquired.

To compare the textures 505 and 507, method 500 performs ROI-to-signal conversion 510 of the textures 505 and 507. As described hereinabove with regard to FIG. 3, method 500 converts each two-dimensional ROI into one-dimensional signals by concatenating the ROI pixel values (e.g., gray values) according to a plurality of pixel-traversing trajectories, including a spiral trajectory, a transpose spiral (T.Spiral) trajectory, a zig-zag trajectory, and a transpose zig-zag (T.Zigzag) trajectory. Thus, for the initial texture 505, the conversion 510 results in four signals 515 comprising different one-dimensional representations of the initial texture 505. Similarly, for the changed texture 507, the conversion 510 results in four signals 517 comprising different one-dimensional representations of the changed texture 507.

Method 500 then decomposes each signal of the four signals 515 and the four signals 517 into different frequency bands (e.g., LF, MF, HF, and TB as described hereinabove), for example using a wavelet transformation such as DWT. As each signal is decomposed into four different signals, method 500 thus generates sixteen signals 525 from the four signals 515 for the initial texture 505 as well as sixteen signals 527 from the four signals 517 for the changed texture 507.

Method 500 then performs AR modeling 530 of the sixteen signals 525 as well as the sixteen signals 527 to estimate, for example, PSDs for each signal. The AR modeling 530 thus results in sixteen signals 535 comprising AR PSD estimates for the sixteen signals 525, as well as sixteen signals 537 comprising AR PSD estimates for the sixteen signals 527. Method 500 calculates correlation coefficients 540 for the sixteen signals 535 and the sixteen signals 537, resulting in correlation coefficients 542 indicating correlation between the sixteen signals 535 and the sixteen signals 537. In particular, the correlation coefficients 542, organized as a set of 4×4 values in some examples, comprise a measure of correlation between the signals with a same frequency band and a same pixel-traversal trajectory. For example, the correlation coefficients 542 include a correlation coefficient indicating correlation between the AR PSD estimates for the spiral LF signals derived from the initial and changed textures 505 and 507, a correlation coefficient indicating correlation between the AR PSD estimates for the spiral MF signals derived from the textures 505 and 507, a correlation coefficient indicating correlation between the AR PSD estimates for the spiral HF signals from the textures 505 and 507, and so on for each combination of frequency band (e.g., LF, MF, HF, TB) and pixel-traversal trajectory (e.g., spiral, transpose spiral, zig-zag, transpose zig-zag).

Method 500 then determines dissimilarity metrics 550 for the correlation coefficients 542, and extracts features 560 from the dissimilarity metrics 550. The features obtained during feature extraction 560 comprise quantitative measures of the changed texture 507 relative to the initial texture 505, which in turn can be linked to a change in the thermal state of the tissue in the ROI. For example, as described hereinabove, the features obtained during feature extraction 560 may be used as input to one or more machine learning algorithms to classify the temperature of the ROI at the time $T_n$.

It should be appreciated that after acquisition of the first ultrasound image during an ultrasound imaging sequence or ultrasound scan session, the changed texture 507 may comprise the same texture as the initial texture 505. Further, after the initial generation of the sixteen signals 535, method 500 may store the sixteen signals 535 for the initial texture 505 in local memory, so that only the changed texture 507 for ultrasound images acquired subsequent to the initial ultrasound image may be processed to obtain the sixteen signals 537.

To illustrate the methods 300, 400, and 500 described hereinabove, FIGS. 6-18 depict an example application of the methods 300, 400, and 500. In particular, FIG. 6 shows a set of ultrasound images 600 depicting regions of interest for ultrasound images of tissue at different thermal states, according to an embodiment. The set of ultrasound images 600 includes a first ultrasound image 602 and a second ultrasound image 622, wherein the second ultrasound image 622 depicts the same anatomical region of a subject being imaged after a given duration during which an ablation procedure is performed. The images 602 and 622 both depict an RF ablation needle 607 within the tissue. Further, the first ultrasound image 602 includes a plurality of ROIs 610, including at least an ROI 612 positioned adjacent to an end of the RF ablation needle 607. Remaining ROIs of the plurality of ROIs 610 are distributed further away from the ROI 612.

Further, the second ultrasound image 622 also includes a plurality of ROIs 630 including at least an ROI 632 positioned adjacent to the end of the RF ablation needle 607. The plurality of ROIs 630 in the second ultrasound image 622 correspond to the plurality of ROIs 610 in the first ultrasound image 602.

The set of ultrasound images 600 further includes an ultrasound image 618 comprising the ROI 612 in the first ultrasound image 602, as well as an ultrasound image 638 comprising the ROI 632 in the second ultrasound image 622. The ultrasound image 618 depicts a lesion in the ROI 612, which is destroyed via RFA in the ultrasound image 638, resulting in the different textures observable in the ultrasound images 618 and 638. As this change in image texture between the images 618 and 638 occurs due to RFA, the difference in texture may be quantified as described herein to correlate the change in texture to a change in temperature.

In particular, as described hereinabove, the ultrasound images 618 and 638 for the initial texture and the changed texture, respectively, may be converted from the two-dimensional representations depicted in FIG. 6 to a plurality of one-dimensional representations. To that end, FIG. 7 shows a set of diagrams depicting example pixel trajectories 700 for image-to-signal conversion of an example region of interest 701. The pixel trajectories 700 includes a spiral trajectory 710, wherein pixel values starting from the image center and spiraling in a counterclockwise direction in the ROI 701 are concatenated to form a one-dimensional signal or vector. The pixel trajectories 700 further include a transpose spiral trajectory 720, also referred to herein as an inverse spiral trajectory 720, which similarly begins at the center of the ROI 701. The pixel trajectories 700 further includes a zig-zag trajectory 730, which starts in a corner of the ROI 701 and traverses along the columns of the ROI 701. Similarly, the pixel trajectories 700 include a transpose zig-zag trajectory 740, also referred to herein as an inverse zig-zag trajectory 740, which starts in a corner of the ROI 701 and traverses along the rows of the ROI 701 as depicted.

Thus, for each ROI of the plurality of ROIs 610 and 630 depicted in FIG. 6, the pixel values may be concatenated into signals according to the pixel trajectories 700, resulting in four signals for each ROI.

For example, FIG. 8 shows a set of graphs 800 illustrating example signals constructed from a single region of interest such as the ROI 612 according to the pixel trajectories 700, while FIG. 9 shows a set of graphs 900 illustrating example signals constructed from a single region of interest such as the ROI 632 according to the pixel trajectories 700. In particular, the set of graphs 800 includes a first graph 810 depicting a spiral signal 812 of the ROI 612 converted according to the spiral trajectory 710, a second graph 820 depicting a zig-zag signal 822 of the ROI 612 converted according to the zig-zag trajectory 730, a third graph 830 depicting a transpose spiral signal 832 of the ROI 612 converted according to the transpose spiral trajectory 720, and a fourth graph 840 depicting a transpose zig-zag signal 842 of the ROI 612 converted according to the transpose zig-zag trajectory 740. Similarly, the set of graphs 900 includes a first graph 910 depicting a spiral signal 912 of the ROI 632 converted according to the spiral trajectory 710, a second graph 920 depicting a zig-zag signal 922 of the ROI 632 converted according to the zig-zag trajectory 730, a third graph 930 depicting a transpose spiral signal 932 of the ROI 632 converted according to the transpose spiral trajectory 720, and a fourth graph 940 depicting a transpose zig-zag signal 942 of the ROI 632 converted according to the transpose zig-zag trajectory 740.

As depicted, the plots in the set of graphs 800 clearly indicate different signal dynamics despite being converted from the same ROI 612. Similarly, the plots in the set of graphs 900 also clearly indicate different dynamics despite being converted from the same ROI 632.

Prior to decomposing each signal into different frequency (or pseudo-frequency) bands as described hereinabove, the signal trend or offset is removed from each signal, for example by calculating a moving average intensity (e.g., gray value) for each signal, and subtracting the moving average intensity from the signal. As an illustrative and non-limiting example, FIG. 10 shows a set of graphs 1000 illustrating signal offset correction for the spiral signal 812 of the ROI 612 depicted in the graph 810, as well as for the spiral signal 912 of the ROI 632 depicted in the graph 910. In particular, the set of graphs 1000 includes a graph 1012 depicting a corrected spiral signal 1014 comprising the spiral signal 812 with offset removed, as well as a graph 1022 depicting a corrected spiral signal 1024 comprising the spiral signal 912 with the offset removed. As depicted, the corrected spiral signals 1014 and 1024 still exhibit the signal dynamics of the spiral signals 812 and 912, respectively, while also improving the suitability of the signals for wavelet decomposition. It should be appreciated that while the offset removal or correction for the spiral signals 812 and 912 is depicted, offset removal is performed for the remaining signals for both ROIs.

After removing the offset from the signals, wavelet decomposition (e.g., DWT) is performed to decompose the corrected signals into a plurality of frequency bands. As an illustrative and non-limiting example, FIG. 11 shows a set of graphs 1100 illustrating an example decomposition of texture signals into pseudo-frequency bands for a first thermal state, according to an embodiment. In particular, the set of graphs 1100 illustrate the decomposition of the corrected spiral signal 1014 obtained from the initial texture of the ROI 612. The set of graphs 1100 includes a first graph 1110 depicting a DWT spiral signal 1112 in the low frequency (LF) band, a second graph 1120 depicting a DWT spiral signal 1122 in the middle frequency (MF) band, a third graph 1130 depicting a DWT spiral signal 1132 in the high frequency (HF) band, and a fourth graph 1140 depicting a DWT spiral signal 1142 in the total frequency band (TB). As discussed hereinabove, the DWT spiral signal 1112 is obtained using scale parameters 6 and 7 for DWT, the DWT spiral signal 1122 is obtained using scale parameters 4 and 5 for DWT, the DWT spiral signal 1132 is obtained using scale parameters 2 and 3 for DWT, and the DWT spiral signal 1142 is obtained using scale parameters 2 through 7 for DWT.

Similarly, FIG. 12 shows a set of graphs 1200 illustrating an example decomposition of texture signals into pseudo-frequency bands for a second thermal state, according to an embodiment. In particular, the set of graphs 1200 illustrate the decomposition of the corrected spiral signal 1024 obtained from the changed texture in the ROI 632. The set of graphs 1200 includes a first graph 1210 depicting a DWT spiral signal 1212 in the low frequency (LF) band, a second graph 1220 depicting a DWT spiral signal 1222 in the middle frequency (MF) band, a third graph 1230 depicting a DWT spiral signal 1232 in the high frequency (HF) band, and a fourth graph 1240 depicting a DWT spiral signal 1242 in the total frequency band (TB). Consistent with the DWT spiral signals of FIG. 11, the DWT spiral signal 1212 is obtained using scale parameters 6 and 7 for DWT, the DWT spiral signal 1222 is obtained using scale parameters 4 and 5 for DWT, the DWT spiral signal 1232 is obtained using scale parameters 2 and 3 for DWT, and the DWT spiral signal 1242 is obtained using scale parameters 2 through 7 for DWT.

Thus, for each conversion type (i.e., each pixel-traversal trajectory for converting the ROIs to signals), the signal is decomposed into four different frequency bands, resulting in sixteen signals given four conversion types. The sixteen signals after decomposition all quantitatively depict the texture of the ROI in different representations, allowing different aspects of the texture which may not be discernable by simple direct observation of the image texture in the ROI, to be clearly defined.

After decomposition of the signals, the decomposed signals are then estimated with an AR model as described hereinabove. As an illustrative and non-limiting example, FIG. 13 shows a set of graphs 1300 illustrating example power spectral density estimates obtained through autoregressive modeling of the decomposed texture signals of FIGS. 11 and 12. The set of graphs 1300 includes a first set of graphs 1305 depicting example power spectral density estimates determined through AR modeling of the DWT spiral signals derived from the ROI 612 and depicted in FIG. 11, as well as a second set of graphs 1355 depicting example power spectral density estimates determined through AR modeling of the DWT spiral signals derived from the ROI 632 and depicted in FIG. 12.

In particular, the first set of graphs 1305 includes a graph 1310 depicting a PSD estimate 1312 determined through AR modeling of the DWT spiral signal 1112 in the LF band. The graph 1310 further depicts a periodogram 1314 generated for the DWT spiral signal 1112. The first set of graphs 1305 further includes a graph 1320 depicting an AR PSD estimate 1322 and a periodogram 1324 for the DWT spiral signal 1122 in the MF band, a graph 1330 depicting an AR PSD estimate 1332 and a periodogram 1334 for the DWT spiral signal 1132 in the HF band, and a graph 1340 depicting an AR PSD estimate 1342 and a periodogram 1344 for the DWT spiral signal 1142 in the TB.

Similarly, the second set of graphs 1355 includes a graph 1360 depicting an AR PSD estimate 1362 and a periodogram 1364 for the DWT spiral signal 1212 in the LF band, a graph 1370 depicting an AR PSD estimate 1372 and a periodogram 1374 for the DWT spiral signal 1222 in the MF band, a graph 1380 depicting an AR PSD estimate 1382 and a periodogram 1384 for the DWT spiral signal 1232 in the HF band, and a graph 1390 depicting an AR PSD estimate 1392 and a periodogram 1394 for the DWT spiral signal 1242 in the TB.

As described hereinabove, a method for thermal monitoring of tissue includes calculating correlation coefficients for signals between an initial texture and a changed texture. As an illustrative example, FIG. 14 shows a set of example correlation coefficient (CC) maps 1400 computed for a plurality of thermal states, according to an embodiment. In particular, the set of CC maps 1400 depict correlation coefficients computed for the ROI 612 over time and thus for a plurality of temperatures of the tissue in the ROI 612. Each CC map of the set of CC maps 1400 depicts a color illustrating a value of a correlation coefficient ranging from zero to one, as indicated by the legend 1480.

The set of CC maps 1400 includes a first CC map 1410 depicting correlation coefficients calculated between AR PSD estimates for the ROI 612 at a first temperature of 27.5° C. In particular, each correlation coefficient is computed for AR PSD estimates with itself, and so each correlation coefficient is one.

The set of CC maps 1400 further includes a second CC map 1420 for the same ROI at a second temperature of 30° C., a third CC map 1430 for the ROI at a third temperature of 40° C., a fourth CC map 1440 for the ROI at a fourth temperature of 50° C., a fifth CC map 1450 for the ROI at a fifth temperature of 60° C., a sixth CC map 1460 for the ROI at a sixth temperature of 70° C., and a seventh CC map 1470 for the ROI at a seventh temperature of 80° C.

As depicted by the CC maps 1400, an increase of dissimilarity for increasing temperature is observed. The CC maps 1410 and 1420, for example, depict a sensitivity for small temperature increases (e.g., from 27.5° C. to 30° C.) in the narrow bands of the transpose spiral (T. Spiral) conversion. The CC maps 1430 and 1440 indicate a slight sensitivity to temperature increase in the zig-zag and transpose zig-zag conversions. The dissimilarities in the narrow bands of the zig-zag and transpose zig-zag conversions are significantly more sensitive, as depicted by CC maps 1450 and 1460, for increasing temperatures at higher temperatures. The dissimilarities in the narrow bands of the spiral conversion also appear to increase with temperatures higher than 70° C., as indicated by the CC map 1470.

While the CC maps 1400 are useful for visually depicting increasing dissimilarities in the sixteen channels derived for a single ROI, and although they may also be useful as features for relating texture changes to temperature changes, a more robust method includes combining the dissimilarities of a CC map, for example, into a dissimilarity metric or dissimilarity vector.

As an illustrative and non-limiting example, FIG. 15 shows a graph 1500 illustrating example dissimilarity vectors of sorted correlation coefficients for different thermal states, according to an embodiment. Each CC map of the CC maps 1400 are sorted by CC values and combined into a dissimilarity vector in the graph 1500. In particular, the graph 1500 includes a dissimilarity vector 1510 comprising the sorted correlation coefficients of the CC map 1410, a dissimilarity vector 1520 comprising the sorted correlation coefficients of the CC map 1420, a dissimilarity vector 1530 comprising the sorted correlation coefficients of the CC map 1430, a dissimilarity vector 1540 comprising the sorted correlation coefficients of the CC map 1440, a dissimilarity vector 1550 comprising the sorted correlation coefficients of the CC map 1450, a dissimilarity vector 1560 comprising the sorted correlation coefficients of the CC map 1460, and a dissimilarity vector 1570 comprising the sorted correlation coefficients of the CC map 1470.

The dissimilarity vector 1510 corresponds to the initial texture at 27.5° C. compared with itself, and thus is a straight line with all correlation coefficients equal to one. An increase of the tissue temperature to 30° C. results in a curvature of the dissimilarity vector 1520 relative to the dissimilarity vector 1510. The curvature of the subsequent dissimilarity vectors 1530, 1540, 1550, and 1560 continues to increase with increasing temperature, as particularly noted by the lowest coefficient (i.e., the first sorted coefficient in the dissimilarity vectors). The dissimilarity vector 1570 indicates a substantial shift in texture dissimilarity from 70° C. (with correlation coefficients depicted in the dissimilarity vector 1560) to 80° C.

As depicted in the graph 1500, the dissimilarity vectors of different temperatures are easily distinguishable. Further, the dissimilarity vectors may be characterized using a variety of features that may be extracted from the dissimilarity vectors.

As one example, FIG. 16 shows a set of graphs 1600 illustrating a first example feature extracted from the dissimilarity vectors of FIG. 15. In particular, the first example feature comprises the mean correlation coefficient of the dissimilarity vectors. The set of graphs 1600 includes a graph 1605 depicting the mean correlation coefficient 1610 for the first dissimilarity vector 1510, the mean correlation coefficient 1612 for the second dissimilarity vector 1520, the mean correlation coefficient 1614 for the third dissimilarity vector 1530, the mean correlation coefficient 1616 for the fourth dissimilarity vector 1540, the mean correlation coefficient 1618 for the fifth dissimilarity vector 1550, and the mean correlation coefficient 1620 for the sixth dissimilarity vector 1560. Similarly, the set of graphs 1600 includes a bar graph 1635 depicting the mean correlation coefficients for the plurality of dissimilarity vectors in terms of their corresponding tissue temperatures. Initially the mean correlation coefficient is one, for the initial texture, and the mean correlation coefficient decreases with increasing temperature.

The median correlation coefficient is another feature that may be extracted from the dissimilarity vectors. As an illustrative example, FIG. 17 shows a set of graphs 1700 illustrating a second example feature extracted from the dissimilarity vectors of FIG. 15. In particular, the second example feature comprises the median correlation coefficient of the dissimilarity vectors. The set of graphs 1700 includes a graph 1705 depicting the median correlation coefficient 1710 for the first dissimilarity vector 1510, the median correlation coefficient 1712 for the second dissimilarity vector 1520, the median correlation coefficient 1714 for the third dissimilarity vector 1530, the median correlation coefficient 1716 for the fourth dissimilarity vector 1540, the median correlation coefficient 1718 for the fifth dissimilarity vector 1550, and the median correlation coefficient 1720 for the sixth dissimilarity vector 1560. Similarly, the set of graphs 1700 includes a bar graph 1735 depicting the median correlation coefficients for the plurality of dissimilarity vectors in terms of their corresponding tissue temperatures. Initially the median correlation coefficient is one, for the initial texture, and the median correlation coefficient decreases with increasing temperature. As depicted, the shift in the median correlation coefficient as a function of temperature is smaller than the corresponding shift in mean correlation coefficient, and combined the two features of median and mean correlation coefficients provide a concise way to relate the image textures of the ROI to temperature.

Additional features may be obtained by determining the linear regression of the dissimilarity vectors. As an illustrative example, FIG. 18 shows a set of graphs 1800 illustrating a third example feature and a fourth example feature extracted from the dissimilarity vectors of FIG. 15. In particular, the set of graphs 1800 includes a graph 1805 depicting example linear regressions of each dissimilarity vector, including a first linear regression 1810 for the dissimilarity vector 1510, a second linear regression 1812 for the dissimilarity vector 1520, a third linear regression 1814 for the dissimilarity vector 1530, a fourth linear regression 1816 for the dissimilarity vector 1540, a fifth linear regression 1818 for the dissimilarity vector 1550, and a sixth linear regression 1820 for the dissimilarity vector 1560. The set of graphs 1800 further includes a graph 1835 depicting the slope of each linear regression in the graph 1805, as well as a graph 1845 depicting the intercept of each linear regression in the graph 1805. As depicted by the graph 1835, the slope increases as temperature increases. Similarly, as depicted by the graph 1845, the intercept decreases as the temperature increases.

Thus, by processing an ROI to obtain a dissimilarity vectors between an initial texture and a changed texture of the ROI, a plurality of features may be extracted from the dissimilarity vector including the mean correlation coefficient of the dissimilarity vector, the median correlation coefficient of the dissimilarity vector, the slope of the linear regression of the dissimilarity vector, and the intercept of the linear regression of the dissimilarity vector. These four features may be used to classify temperature ranges for each changed texture, as described hereinabove.

The one or more machine learning algorithms described hereinabove may be trained to classify temperature of tissue based on such features. For example, a training dataset for training the one or more machine learning algorithms may include the four extracted features and a label for each combination of features. The label may indicate the temperature of the tissue texture, which may be measured during creation of the training dataset by use of optical fibers or another device for measuring exact temperature of the ROIs. Additionally or alternatively, the label may indicate a value corresponding to a temperature range. For example, the label may comprise 0 for temperatures below 60° C., and 1 for temperatures equal to or above 60° C. The training dataset may be rearranged with random permutations to shuffle the rows, and furthermore split into two parts (e.g., a first part including 75% of the dataset and a second part including 25% of the dataset) for training and testing. As mentioned hereinabove, the one or more machine learning algorithms may include one or more of a random forest classifier (RFC), a support vector machine (SVM), an artificial neural network (ANN), and other machine learning algorithms suitable for classification.

A technical effect of the present disclosure includes the acquisition of an ultrasound image. Another technical effect of the present disclosure includes the classification of a temperature of tissue depicted in an ultrasound image. Yet another technical effect of the present disclosure includes the display of a thermal state of tissue based on analysis of an ultrasound image. Another technical effect of the present disclosure includes the quantitative assessment of image texture in an ultrasound image relative to a previously-acquired ultrasound image.

In one embodiment, a method comprises acquiring, via an ultrasound probe, an ultrasound image, selecting at least one region of interest in the ultrasound image, extracting features from the at least one region of interest, classifying a thermal state of tissue in the at least one region of interest based on the features, and outputting, via a display device, the thermal state of the tissue.

In a first example of the method, extracting the features from the at least one region of interest comprises converting the at least one region of interest to at least one signal, decomposing the at least one signal into multiple frequency bands, generating an estimate for each decomposed signal with an autoregressive model, calculating a correlation coefficient for each estimate with an initial estimate in a same frequency band, determining a dissimilarity metric based on the correlation coefficient for each estimate, and extracting the features from the dissimilarity metric. In a second example of the method optionally including the first example, the features comprise one or more of a median correlation coefficient of the dissimilarity metric, a mean correlation coefficient of the dissimilarity metric, a slope of a linear regression of the dissimilarity metric, and an intercept of a linear regression of the dissimilarity metric. In a third example of the method optionally including one or more of the first and second examples, converting the at least one region of interest to the at least one signal comprises, for a region of interest of the at least one region of interest, sampling pixel values of the region of interest while traversing pixels of the region of interest along a plurality of pixel trajectories to generate a plurality of signals for the region of interest, each signal of the plurality of signals corresponding to a different pixel trajectory of the plurality of pixel trajectories. In a fourth example of the method optionally including one or more of the first through third examples, decomposing the at least one signal into multiple frequency bands comprises decomposing, using a discrete wavelet transform, the at least one signal into the multiple frequency bands. In a fifth example of the method optionally including one or more of the first through fourth examples, generating the estimate for each decomposed signal with the autoregressive model comprises performing autoregressive modeling of each decomposed signal to obtain an autoregressive parameter for each decomposed signal, and calculating a power spectral density for each decomposed signal based on the respective autoregressive parameter, the estimate comprising the power spectral density. In a sixth example of the method optionally including one or more of the first through fifth examples, the method further comprises calculating the correlation coefficient for each estimate with the initial estimate in the same frequency band and a same image-to-signal conversion type. In a seventh example of the method optionally including one or more of the first through sixth examples, determining the dissimilarity metric based on the correlation coefficient for each estimate comprises sorting the correlation coefficients for the estimates into a vector, and extracting the features from the at least one region of interest comprises calculating the features from the vector. In an eighth example of the method optionally including one or more of the first through seventh examples, classifying the thermal state of the tissue in the at least one region of interest based on the features comprises inputting the features into one or more machine learning algorithms, and receiving, from the one or more machine learning algorithms, a classification of the thermal state of the tissue. In a ninth example of the method optionally including one or more of the first through eighth examples, the classification comprises one or more of a classification of temperature or a classification of tissue damage reversibility. In a tenth example of the method optionally including one or more of the first through ninth examples, selecting the at least one region of interest in the ultrasound image comprises selecting a first region of interest at an ablation target in the ultrasound image, and selecting a plurality of additional regions of interest in the ultrasound image positioned away from the ablation target.

In another embodiment, a method comprises acquiring, with an ultrasound probe, an ultrasound image, converting a region of interest in the ultrasound image to a plurality of signals, decomposing each signal of the plurality of signals into a plurality of frequency bands, generating an estimate for each decomposed signal with an autoregressive model for each frequency band of the plurality of frequency bands, measuring a correlation of the estimate for each decomposed signal with a corresponding estimate obtained from a previously-acquired ultrasound image, calculating a plurality of features based on the correlation for each decomposed signal, classifying, with a machine learning algorithm based on the plurality of features, a thermal state of tissue in the region of interest, and outputting, via a display device, the thermal state of the tissue.

In a first example of the method, converting the region of interest to the plurality of signals comprises sampling pixel values of the region of interest with a plurality of pixel-traversing trajectories to generate the plurality of signals. In a second example of the method optionally including the first example, decomposing each signal of the plurality of signals into the plurality of frequency bands comprises applying a discrete wavelet transform to each signal to decompose each signal into a low-frequency band signal, a middle-frequency band signal, a high-frequency band signal, and a total frequency band signal. In a third example of the method optionally including one or more of the first and second examples, the plurality of features includes one or more of a median correlation coefficient, a mean correlation coefficient, a slope of a linear regression of a vector including the correlation of each decomposed signal, and an intercept of the linear regression of the vector. In a fourth example of the method optionally including one or more of the first through third examples, classifying, with the machine learning algorithm based on the plurality of features, the thermal state of the tissue in the region of interest comprises classifying a temperature of the tissue relative to a critical ablation temperature.

In yet another embodiment, a system comprises an ultrasound probe, a display device, and a processor configured with executable instructions in non-transitory memory that when executed cause the processor to: acquire, via the ultrasound probe, an ultrasound image; select at least one region of interest in the ultrasound image; extract features from the at least one region of interest; classify a thermal state of tissue in the at least one region of interest based on the features; and output, via the display device, the thermal state of the tissue.

In a first example of the system, the processor is further configured with executable instructions in the non-transitory memory that when executed cause the processor to: convert the at least one region of interest to a plurality of signals; decompose each signal of the plurality of signals into a plurality of frequency bands; generate an estimate for each decomposed signal with an autoregressive model; calculate a correlation coefficient for each estimate with an initial estimate obtained from a previously-acquired ultrasound image in a same frequency band; determine a dissimilarity metric based on the correlation coefficient for each estimate; and extract the features from the dissimilarity metric. In a second example of the system optionally including the first example, the features comprise one or more of a mean correlation coefficient, a median correlation coefficient, a slope of a linear regression of the dissimilarity metric, and an intercept of the linear regression of the dissimilarity metric. In a third example of the system optionally including one or more of the first and second examples, the processor is further configured with executable instructions in the non-transitory memory that when executed cause the processor to: classify, with a machine learning algorithm based on the plurality of features, the thermal state of the tissue in the region of interest, the thermal state comprising a temperature of the tissue relative to a critical ablation temperature.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring, via an ultrasound probe, an ultrasound image;
   selecting at least one region of interest in the ultrasound image;
   extracting features from the at least one region of interest, wherein extracting the features from the at least one region of interest comprises:
     converting the at least one region of interest to at least one signal;
     decomposing the at least one signal into multiple frequency bands;
     generating an estimate for each decomposed signal with an autoregressive model;
     calculating a correlation coefficient for each estimate with an initial estimate in a same frequency band;
     determining a dissimilarity metric based on the correlation coefficient for each estimate; and
     extracting the features from the dissimilarity metric;
   classifying a thermal state of tissue in the at least one region of interest based on the features; and
   outputting, via a display device, the thermal state of the tissue.

2. The method of claim 1, wherein the features comprise one or more of a median correlation coefficient of the dissimilarity metric, a mean correlation coefficient of the dissimilarity metric, a slope of a linear regression of the dissimilarity metric, and an intercept of a linear regression of the dissimilarity metric.

3. The method of claim 1, wherein converting the at least one region of interest to the at least one signal comprises, for a region of interest of the at least one region of interest, sampling pixel values of the region of interest while traversing pixels of the region of interest along a plurality of pixel trajectories to generate a plurality of signals for the region of interest, each signal of the plurality of signals corresponding to a different pixel trajectory of the plurality of pixel trajectories.

4. The method of claim 1, wherein decomposing the at least one signal into multiple frequency bands comprises decomposing, using a discrete wavelet transform, the at least one signal into the multiple frequency bands.

5. The method of claim 1, wherein generating the estimate for each decomposed signal with the autoregressive model comprises performing autoregressive modeling of each decomposed signal to obtain an autoregressive parameter for each decomposed signal, and calculating a power spectral density for each decomposed signal based on the respective autoregressive parameter, the estimate comprising the power spectral density.

6. The method of claim 1, further comprising calculating the correlation coefficient for each estimate with the initial estimate in the same frequency band and a same image-to-signal conversion type.

7. The method of claim 1, wherein determining the dissimilarity metric based on the correlation coefficient for each estimate comprises sorting the correlation coefficients for the estimates into a vector, and wherein extracting the features from the at least one region of interest comprises calculating the features from the vector.

8. The method of claim 1, wherein classifying the thermal state of the tissue in the at least one region of interest based on the features comprises inputting the features into one or more machine learning algorithms, and receiving, from the one or more machine learning algorithms, a classification of the thermal state of the tissue.

9. The method of claim 8, wherein the classification comprises one or more of a classification of temperature or a classification of tissue damage reversibility.

10. The method of claim 1, wherein selecting the at least one region of interest in the ultrasound image comprises selecting a first region of interest at an ablation target in the ultrasound image, and selecting a plurality of additional regions of interest in the ultrasound image positioned away from the ablation target.

11. A method, comprising:
    acquiring, with an ultrasound probe, an ultrasound image;
    converting a region of interest in the ultrasound image to a plurality of signals;
    decomposing each signal of the plurality of signals into a plurality of frequency bands;
    generating an estimate for each decomposed signal with an autoregressive model for each frequency band of the plurality of frequency bands;
    measuring a correlation of the estimate for each decomposed signal with a corresponding estimate obtained from a previously-acquired ultrasound image;
    calculating a plurality of features based on the correlation for each decomposed signal;
    classifying, with a machine learning algorithm based on the plurality of features, a thermal state of tissue in the region of interest; and outputting, via a display device, the thermal state of the tissue.

12. The method of claim 11, wherein converting the region of interest to the plurality of signals comprises sampling pixel values of the region of interest with a plurality of pixel-traversing trajectories to generate the plurality of signals.

13. The method of claim 11, wherein decomposing each signal of the plurality of signals into the plurality of frequency bands comprises applying a discrete wavelet transform to each signal to decompose each signal into a low-frequency band signal, a middle-frequency band signal, a high-frequency band signal, and a total frequency band signal.

14. The method of claim 11, wherein the plurality of features includes one or more of a median correlation coefficient, a mean correlation coefficient, a slope of a linear regression of a vector including the correlation of each decomposed signal, and an intercept of the linear regression of the vector.

15. The method of claim 11, wherein classifying, with the machine learning algorithm based on the plurality of features, the thermal state of the tissue in the region of interest comprises classifying a temperature of the tissue relative to a critical ablation temperature.

16. A system, comprising:
   an ultrasound probe;
   a display device; and
   a processor configured with executable instructions in non-transitory memory that when executed cause the processor to:
   acquire, via the ultrasound probe, an ultrasound image;
   select at least one region of interest in the ultrasound image;
   extract features from the at least one region of interest;
   convert the at least one region of interest to a plurality of signals;
   decompose each signal of the plurality of signals into a plurality of frequency bands;
   generate an estimate for each decomposed signal with an autoregressive model;
   calculate a correlation coefficient for each estimate with an initial estimate obtained from a previously-acquired ultrasound image in a same frequency band;
   determine a dissimilarity metric based on the correlation coefficient for each estimate;
   extract the features from the dissimilarity metric;
   classify a thermal state of tissue in the at least one region of interest based on the features; and
   output, via the display device, the thermal state of the tissue.

17. The system of claim 16, wherein the features comprise one or more of a mean correlation coefficient, a median correlation coefficient, a slope of a linear regression of the dissimilarity metric, and an intercept of the linear regression of the dissimilarity metric.

18. The system of claim 16, wherein the processor is further configured with executable instructions in the non-transitory memory that when executed cause the processor to: classify, with a machine learning algorithm based on the plurality of features, the thermal state of the tissue in the region of interest, the thermal state comprising a temperature of the tissue relative to a critical ablation temperature.

* * * * *